US009522162B2

(12) United States Patent
Prestwich et al.

(10) Patent No.: US 9,522,162 B2
(45) Date of Patent: Dec. 20, 2016

(54) METHODS FOR TREATING OR PREVENTING UROLOGICAL INFLAMMATION

(75) Inventors: Glenn D. Prestwich, Eastsound, WA (US); Siam Oottamasathien, VIII, Salt Lake City, UT (US); Wanjian Jia, Salt Lake City, UT (US); Lindsi McCoard, Salt Lake City, UT (US); Won Yong Lee, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 31 days.

(21) Appl. No.: 14/006,771

(22) PCT Filed: Mar. 23, 2012

(86) PCT No.: PCT/US2012/030233
§ 371 (c)(1),
(2), (4) Date: Jul. 22, 2014

(87) PCT Pub. No.: WO2012/129461
PCT Pub. Date: Sep. 27, 2012

(65) Prior Publication Data
US 2014/0343011 A1 Nov. 20, 2014

Related U.S. Application Data

(63) Continuation-in-part of application No. PCT/US2011/039550, filed on Jun. 8, 2011, which is a continuation-in-part of application No. 13/069,860, filed on Mar. 23, 2011, now Pat. No. 8,343,942.

(51) Int. Cl.
| | |
|---|---|
| A61K 31/728 | (2006.01) |
| A61K 31/737 | (2006.01) |
| C08B 37/08 | (2006.01) |
| A61K 45/06 | (2006.01) |
| A23L 2/38 | (2006.01) |
| A23L 2/52 | (2006.01) |
| A61K 9/00 | (2006.01) |

(52) U.S. Cl.
CPC ............ *A61K 31/728* (2013.01); *A23L 2/38* (2013.01); *A23L 2/52* (2013.01); *A61K 31/737* (2013.01); *A61K 45/06* (2013.01); *C08B 37/0072* (2013.01); *A23V 2002/00* (2013.01); *A61K 9/0034* (2013.01)

(58) Field of Classification Search
None
See application file for complete search history.

(56) References Cited

U.S. PATENT DOCUMENTS

| | | | |
|---|---|---|---|
| 2,599,172 | A | 6/1952 | Hadidian |
| 4,240,163 | A | 12/1980 | Galin |
| 4,814,437 | A | 3/1989 | De Belder |
| 4,851,521 | A | 7/1989 | Della Valle |
| 5,008,253 | A | 4/1991 | Casu |
| 5,166,331 | A | 11/1992 | Della Valle |
| 5,442,053 | A | 8/1995 | Della Valle |
| 5,559,104 | A | 9/1996 | Romeo |
| 5,981,509 | A | 11/1999 | Akima |
| 6,288,043 | B1 | 9/2001 | Spiro |
| 6,339,074 | B1 | 1/2002 | Cialdi |
| 6,803,037 | B2 | 10/2004 | Abatangelo |
| 6,828,308 | B2 | 12/2004 | Mastradonato |
| 6,833,363 | B2 | 12/2004 | Renier |
| 7,202,230 | B2 | 4/2007 | Rivarossa |
| 7,683,038 | B2 | 3/2010 | Bellini |
| 7,855,187 | B1 | 12/2010 | Prestwich |
| 8,329,673 | B2 | 12/2012 | Prestwich |
| 8,343,942 | B2 | 1/2013 | Oottamasathien |
| 8,399,430 | B2 | 3/2013 | Prestwich |
| 2002/0049183 | A1 | 4/2002 | Yedgar |
| 2003/0198599 | A1 | 10/2003 | Yalpani |
| 2003/0199687 | A1 | 10/2003 | Yalpani |
| 2004/0053885 | A1 | 3/2004 | Venbrocks |
| 2005/0119219 | A1 | 6/2005 | Bellini |
| 2005/0203056 | A1 | 9/2005 | Ulmer |
| 2006/0172967 | A1 | 8/2006 | Toida |

(Continued)

FOREIGN PATENT DOCUMENTS

| | | |
|---|---|---|
| DE | 19813234 | 9/1999 |
| DE | 102005004643 | 8/2006 |

(Continued)

OTHER PUBLICATIONS

Zaneveld, L. et al "Use of mandelic acid condensation polymer . . . " Fertil. Steril. (2002) vol. 78, No. 5, pp. 1107-1115.*
Haase, A. "Peril at mucosal front lines for HIV . . . " Nature Rev. Immunol. (2005) vol. 5, pp. 783-792.*
Ogawa, D., et al. "Sulfated Hyaluronic Acid, a Potential Selectin Inhibitor, Ameliorates Experimentally Induced Crescentic Glomerulonephritis," Experimental Nephrology, 2005, 99:e26-e32.
Matsuda, M., et a. "Therapeutic effect of sulphated hyaluronic acid, a potential selectin-blocking agent, on experimental progressive mesangial proliferative glomerulonephritis," J. Pathol., 2002, 198:407-414.
Extended European Search Report for European application No. 12761460.0 dated Aug. 27, 2014.

(Continued)

*Primary Examiner* — Leigh C Maier
(74) *Attorney, Agent, or Firm* — Gardner Groff Greenwald & Villanueva, PC

(57) ABSTRACT

Described herein are methods for treating or preventing urological inflammation in a subject comprising administering to the subject an effective amount of a compound comprising a. a modified hyaluronan or a pharmaceutically acceptable salt or ester thereof, wherein said hyaluronan or its pharmaceutically acceptable salt or ester comprises at least one sulfate group and at least one primary C-6 hydroxyl position of an N-acetyl-glucosamine residue comprising an alkyl group or fluoroalkyl group; b. a partially or fully sulfated hyaluronan or the pharmaceutically acceptable salt or ester thereof, or a combination thereof.

11 Claims, 18 Drawing Sheets

(56) References Cited

U.S. PATENT DOCUMENTS

| | | |
|---|---|---|
| 2006/0223781 A1 | 10/2006 | Guo |
| 2007/0054878 A1 | 3/2007 | Venbrocks |
| 2008/0025950 A1 | 1/2008 | Prestwich |
| 2008/0032920 A1 | 2/2008 | Prestwich |
| 2008/0050335 A1 | 2/2008 | Faour |
| 2008/0182982 A1 | 7/2008 | Kumar |
| 2008/0306022 A1 | 12/2008 | Miyamoto |
| 2008/0306023 A1 | 12/2008 | Rinaudo |
| 2009/0105463 A1 | 4/2009 | Berry |
| 2009/0197807 A1 | 8/2009 | Callegaro |
| 2009/0202639 A1 | 8/2009 | Bellini |
| 2009/0226499 A1 | 9/2009 | Wisniewski |
| 2009/0252810 A1 | 10/2009 | Tommeraas |
| 2009/0285850 A1 | 11/2009 | Dillon |
| 2010/0204325 A1 | 8/2010 | Blanda |
| 2010/0278877 A1 | 11/2010 | Tamura |
| 2010/0317616 A1 | 12/2010 | Prestwich |
| 2011/0082104 A1 | 4/2011 | Prestwich |
| 2013/0190234 A1 | 7/2013 | Prestwich |

FOREIGN PATENT DOCUMENTS

| | | |
|---|---|---|
| EP | 0244178 | 11/1987 |
| EP | 0285357 | 10/1989 |
| EP | 0214879 | 11/1990 |
| EP | 0889055 | 4/2000 |
| EP | 0601055 | 6/2000 |
| EP | 0925310 | 8/2000 |
| EP | 0754460 | 6/2002 |
| EP | 1169387 | 3/2003 |
| EP | 1022289 | 7/2004 |
| EP | 1365777 | 4/2006 |
| EP | 1087797 | 7/2009 |
| EP | 1994062 | 7/2009 |
| EP | 1901786 | 12/2010 |
| EP | 1144459 | 2/2011 |
| FR | 2864090 | 6/2005 |
| JP | 11279042 | 10/1999 |
| JP | 2001097997 | 4/2001 |
| JP | 2001163789 | 6/2001 |
| WO | 8907932 | 9/1989 |
| WO | 9943728 | 9/1999 |
| WO | 2004004744 | 1/2004 |
| WO | 2005056608 | 6/2005 |
| WO | 2007006403 | 1/2007 |
| WO | 2007043050 | 4/2007 |
| WO | 2008008859 | 1/2008 |
| WO | 2005046562 A3 | 12/2008 |
| WO | 2009013162 | 1/2009 |
| WO | 2009059748 | 9/2009 |
| WO | 2009124266 | 12/2009 |
| WO | 2010087207 | 8/2010 |
| WO | 2010121700 | 10/2010 |
| WO | 2010130466 | 11/2010 |
| WO | 2010130468 | 11/2010 |

OTHER PUBLICATIONS

English Summary of Notice of Rejection from Japanese Patent Office for Application 2014-501262 dated Jan. 15, 2016.
Abtangelo et al., "Biocompatibility and enzymatic degradation studies on sulphated hyaluronic acid derivatives," Biomaterials, 1997, 18:1411-1415.
Allmen et al., "V domain of RAGE interacts with AGEs on prostate carcinoma cells," The Prostate, 2008, 68:748-758.
Anderson et al., "Pentosan polysulfate: a review of its use in the relief of bladder pain or discomfort in interstitial cystitis," Drugs, 2006, 66:821-835.
Barbucci, "Low- and high-resolution nuclear magnetic resonance (NMR) characterisation of hyaluronan-based native and sulfated hydrogels," Carbohydrate Res., 2006, 341:1848-1858.
Baykal et al., "Intravesical heparin and peripheral neuromodulation on interstitial cystitis," Urol. Int., 2005, 74:361-364.
Benck et al., "Proteinuria-lowering effect of heparin therapy in diabetic nephropathy without affecting the renin-angiotensin-aldosterone system," Clin. J. Am. Soc. Nephrol., 2007, 2:58-67.
Benesova et al.,"Stability evaluation of n-alkyl hyaluronic acid derivatives by DSC and TG measurement," J. Therm. Analys. Calorim., 2006, 83:341-348.
Benitez et al., "Targeting hyaluronidase for cancer therapy: antitumor activity of sulfated hyaluronic acid in prostate cancer cells," Canc. Res., 2011, 71:4085-4095.
Bohlender et al., "Advanced glycation end products in the kidney," Am. J. Renal Physiol., 2005, 289:F645-F659.
Cen et al., "Assessment of in vitro Bioactivity of Hyaluronic Acid and Sulfated Hyaluronic Acid Functionalied Electroactive Polymer," Biomacromolecules, 2004, 5:2238-2246.
Cheng et al., "Expression profiling of endogenous secretory receptor for advanced glycation end products in human organs," Modern Pathol., 2005, 18:1385-1396.
Dausse et al., "Cartilage Repair Using New Polysaccharidic Biomaterials: Macroscopic, Histological and Biochemical Approaches in a Rat Model of Cartilage Defect," Osteoarthritis and Cartilage, 2003, 11:16-28.
Hammer, "Viscous corneal protection by sodium hyaluronate, chondroitin sulfate, and methylcellulose," Invest. Ophthalmol. Vis. Sci., 1984, 25:1329-1332.
Hermani et al., "Calcium-binding proteins S100A8 and S100A9 as Novel Diagnostic Markers in Human Prostate Cancer," Clin. Cancer Res., 2005, 11:5146-5152.
Iavazzo et al., "Hyaluronic acid: an effective alternative treatment of interstitial cystitis, recurrent urinary tract infections, and hemorrhagic cystitis?" Europ. Urol., 2007, 51:1534-1541.
Ishiguro et al., "Receptor for advanced glycation end products (RAGE) and its ligand, amphoterin are overexpressed and associated with prostate cancer development," The Prostate, 2005, 64:92-100.
Jeanloz, "The methyl ester of methylated hyaluronic acid," J. Biol. Chem., 1952, 197:141-150.
Jones et al., "Epidemiology of interstitial cystitis," Urology, 1997, 49 (5A Suppl.):2-9.
Kaye et al., "Methylation studies on hyaluronic acid," Biochem. J., 1951, 48:249.
Kyyronen, "Methylpridnisolone esters of hyaluronic acid in ophthalmic drug delivery: in vitro and in vivo release studies," Int. J. Pharmaceutics, 1992, 80:161-169.
Limberg et al., "Topical application of hyaluronic acid and chondroitin sulfate in the treatment of dry eyes," Am. J. Ophthalmol., 1987, 103:194-197.
Lukban et al., "Current management of interstitial cystitis," Urol. Clin. N. Am., 2002, 29:649-660.
Macrae et al., "The effects of sodium hyaluronate, chondroitin sulfate, and methylcellulose on the corneal endothelium and intraocular pressure," Am. J. Ophthalmol., 1983, 95:332-41.
Mracek et al., "The Diffusion Process of Sodium Hyaluronate (Na—HA) and Na—HA-n-alkyl Derivatives Films Swelling," J. Biomed. Mater. Res. Part A, 2007, 83A/1:184-190.
Myint et al., "RAGE Control of Diabetic Nephropathy in a Mouse Model: Effects of RAGE Gene Disruption and Administration of Low-Molecular Weight Heparin," Diabetes, 2006, 55:2510-2522.
Nagira et al., "Effects of sulfated hyaluronan on keratinocyte differentiation and Wnt and Notch gene expression," Biomaterials, 2007, 2:844-850.
Nakamura et al., "Concentration and molecular weight dependency of rabbit corneal epithelial wound healing on hyaluronan," Curr. Eye Res., 1992, 11:981-986.
Nepp et al., "The clinical use of viscoelastic artificial tears and sodium chloride in dry-eye syndrome," Biomaterials, 2001, 22:3305-3310.
Parsons et al., "Treatment of interstitial cystitis with intravesical heparin," Br. J. Urol., 1994, 73:504-507.
Parsons, "Successful downregulation of bladder sensory nerves with combination of heparin and alkalinized lidocaine in patients with interstitial cystitis," Urology, 2005, 74:45-48.
Payne et al., "Interstitial cystitis and painful bladder syndrome," J. Urol., 2007, 177:2042-9.

(56) References Cited

OTHER PUBLICATIONS

Sant et al., "A pilot clinical trial of oral pentosan polysulfate and oral hydroxyzine in patients with interstitial cystitis," J. Urol., 2003, 170:810-815.

Satoh et al., "The Basic Research on Physiological Property of Functionalized Hyaluronan (II): Effect of Sulfated Hyaluronan on Histamine Release from the Mast Cell," Fiber, 2004, 60:137-143.

Satoh et al., "The research on physiological property of funcitonalized hyaluronan: interaction between sulfated hyaluronan and plasma proteins," Polymers for Advanced Technologies, 2004, 15:720-725.

SBIR Award ID:93482. "Sulfated Polysaccharide Derivatives for the Treatment of Rosacea," Glycomira, 2009, Abstract only. <http://www.sbir.gov/sbirsearch/detail/192860>.

SBIR Award ID:93781. "Sulfated Polysaccharide Derivatives for the Treatment of Macular Degeneration," Glycomira, 2009, Abstract only. <http://www.sbir.gov/sbirsearch/detail/192862>.

Steinhoff et al., "The efficacy of chondroitin sulfate 0.2% in treating interstitial cystitis," Can. J. Urol., 2002, 9:1454-1458.

Suzuki et al., "Preparation and inhibitory activity on hyaluronidase of fully O-sulfated hyaluro-oligosaccharides," Glycobiol., 2001, 11:57-64.

Talman et al., "Ocular changes induced by polysaccharides. II. Detection of hyaluronic acid sulfate after injection into ocular tissues," Am. J. Ophthalmol., 1959, 47:428-437.

Talman et al., "Ocular changes induced by polysaccharides. III. Paper chromatographic fractionation of a biologically active hyaluronic acid sulfate preparation," Am. J. Ophthalmol., 1959, 48:560-572.

Theoharides et al., "A pilot open label of CystoProtek in interstitial cystitis," Int. J. Immunopathol. Pharmacol., 2005, 18:183-188.

Theoharides et al., "Critical role of mast cells in inflammatory diseases and the effect of acute stress," J. Neuroimmunol., 2004, 146:1-12.

Theoharides et al., "New agents for the medical treatment of interstitial cystitis," Expert Opin. Investig. Drugs, 2001, 10:521-546.

Theoharides, "Treatment approaches for painful bladder syndrome/interstitial cystitis," Drugs, 2007, 67:215-235.

Toft et al., "Recent developments of intravesical therapy of painful bladder syndrome/interstitial cystitis: a review," Curr. Opin. Urol., 2006, 16:268-272.

US Office Action for U.S. Appl. No. 12/870,763 dated Sep. 17, 2010.

US Office Action for U.S. Appl. No. 12/870,774 dated Jul. 17, 2012.

US Office Action for U.S. Appl. No. 12/870,774 dated Mar. 5, 2012.

US Office Action for U.S. Appl. No. 13/069,860 dated Mar. 29, 2012.

US Office Action for U.S. Appl. No. 13/304,292 dated Feb. 21, 2012.

International Search Report for PCT/US09/39498 dated Oct. 29, 2009.

International Search Report for PCT/US12/30233 dated Jul. 3, 2012.

IPRP for PCT/US09/39498 dated Dec. 8, 2010.

Written Opinion of the ISA for PCT/US09/039498 dated Apr. 10, 2010.

\* cited by examiner

METHODS FOR TREATING OR PREVENTING UROLOGICAL INFLAMMATION

CROSS REFERENCE TO RELATED APPLICATIONS

This is a U.S. national phase application under 35 U.S.C §371 of international application no. PCT/US12/030233 filed on Mar. 23, 2012, which claims priority to (1) U.S. nonprovisional application Ser. No. 13/069,860, filed Mar. 23, 2011 and (2) International Application No. PCT/US11/039550, filed Jun. 8, 2011. These applications are hereby incorporated by reference in their entireties for all of their teachings.

ACKNOWLEDGEMENT

This invention was made with government support under Grants T32 HL079874 and DK093413 awarded by the National Institutes of Health. The government has certain rights in the invention.

BACKGROUND

Urological inflammation is a significant health concern for many individuals. For example, neurogenic bladder (NGB) disease can result from excess inflammation that leads to subsequent fibrosis of the urinary bladder. In children, many congenital diseases result in NGB disease, including posterior urethral valves, bladder/cloacal exstrophy, and myelomeningocele (MMC)/Spina Bifida. NGB disease still remains one of the most common causes of renal failure and renal transplantation in children. These processes in children share overlap in adults, in whom chronic inflammatory bladder disorders such as interstitial cystitis (IC), results in significant pelvic pain and debilitating urinary symptoms. More than 4 million people in the United States have IC, with the bulk involving primarily women. The underlying physiology is based on inflammation, but the exact etiology remains elusive. Recently, the cost and disease burden associated with IC was analyzed by the Urologic Diseases in America Project and found to exceed $750 million dollars annually. Presently, the treatment of this condition has been suboptimal because of its uncertain cause and pathogenesis. A fundamental lack of understanding of the inflammatory cascades that perpetuate the disease process has resulted in a paucity of therapeutic options.

Painful bladder syndrome/interstitial cystitis (PBS/IC) is an indolent bladder disorder that has continued to be a debilitating disease with few truly effective treatment options.[1-4] Affecting primarily women, PBS/IC is a chronic disease characterized by urinary frequency, bladder pain, nocturia, urgency, and pelvic pain. While the underlying physiology is based on inflammation, the disease etiology is multifactorial;[4] contributing mechanisms include deficiencies in the GAG layer and mast cell-mediated neuroinflammation.[5] In 1997, PBS/IC was estimated to affect approximately 1 million people in the United States;[6] more recent estimates range from 0.1%-1% of all women.[2] Recently, the cost and disease burden associated with PBS/IC was analyzed by the Urologic Diseases in America Project and found to exceed $750 million dollars annually.[7]

Two anti-inflammatory sulfated polysaccharides are currently available medical therapeutics, but neither is particularly effective. First, heparin is administered intravesically, but off-target effects, expense, and modest efficacy limit its regular usage.[8-10] Second, oral Elmiron (pentosan polysulfate), alleged to replenish the GAG layer, has a long lead time for onset of efficacy, is only effective in <50% of women, is poorly bioavailable (<6% of ingested) to the bladder, and has many undesirable off-target effects.[11,12] Two other treatments include intravesical instillation of Cystistat[13] (unmodified 0.04% hyaluronic acid, HA), and CystoProtek,[14,15] or 0.2% chondroitin sulfate. Options for management of PBS/IC include oral hydroxyzine, quercetin, amitriptyline, gabapentin, and narcotics; intravesical DMSO, resiniferatoxin and botox have also been used, as well as combination therapies.[2-4] Reviews of therapeutic options agree that more effective treatments are needed.[2,3]

In order for the bladder to store urine it must be compliant (pliable). This means it is imperative to hold variable volumes of urine at low pressures. Failure results in elevated bladder pressure, transmitting urine to the kidney resulting in glomerular injury, renal parenchymal fibrosis and renal failure. Excess deposition of extracellular matrix (ECM) within the bladder wall is the main mechanism for loss of bladder wall pliability. This fibrosis can result from multiple mechanisms, one of which includes chronic inflammation. In response, bladder fibrosis is part of a wound healing process with accumulation of ECM proteins (collagen types I and III). Also, during chronic tissue inflammation, damage to fibroblasts and myofibroblasts activates cell proliferation, motility, contractility, and ECM synthesis. The final result is fibrosis, loss of compliance, and bladder dysfunction Other conventionally accepted treatments of inflammation may involve UV phototherapy, corticosteroids and glucocorticoids, acitretin, cyclosporine, and methotrexate. However, each of these treatments may cause serious side effects ranging from immune suppression and liver disease to thinning skin and causing birth defects. Due to partial or complete ineffectiveness, these treatments often leave patients unsatisfied with their results.

As indicated above, heparin treatment has also been experimentally explored. Heparin, a sulfated polysaccharide, has traditionally been used almost exclusively as an anti-coagulant, but its anti-inflammatory properties are well known. Heparin and its derivatives have shown some promise in treating these inflammatory diseases. Particularly heparin and its derivatives disrupt at least three important events in inflammatory cascades. First, heparin attaches to and blocks the leukocyte integrins P- and L-selectin. Second, heparin and its derivatives reduce the inflammatory cascade by binding to and inhibiting the cationic PMN protease human leukocyte elastase and cathepsin G, which reduces proteolytic tissue injury by PMNs that escape the first heparin barrier of selectin inhibition. Third, heparin and its derivatives potentially inhibit the interaction of the receptor for advanced glycation end-products (RAGE) with its ligands.

Although heparin and its derivatives have shown promise in treating inflammation, treatment with heparin and its derivatives exhibits several major drawbacks. First, heparin and its derivatives are porcine-derived; thus leading to concerns of cross-species transfer of viruses. Second, because of heparin's anticoagulant properties, diabetics treated with this compound are at risk of excessive bleeding. Third, heparin may induce thrombocytopenia in certain individuals who produce an antibody to the complex of heparin with the cationic protein platelet factor-4 (PF-4), resulting in catastrophic platelet aggregation and generalized paradoxical arterial and venous clotting. Thus, an important unmet need is to formulate compounds which may be used to treat urological inflammation while avoiding the myriad of side effects seen in other treatments.

SUMMARY

Described herein are methods for treating or preventing urological inflammation in a subject comprising administering to the subject an effective amount of a compound comprising a. a modified hyaluronan or a pharmaceutically acceptable salt or ester thereof, wherein said hyaluronan or its pharmaceutically acceptable salt or ester comprises at least one sulfate group and at least one primary C-6 hydroxyl position of an N-acetyl-glucosamine residue comprising an alkyl group or fluoroalkyl group;

b. a partially or fully sulfated hyaluronan or the pharmaceutically acceptable salt or ester thereof, or a combination thereof.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
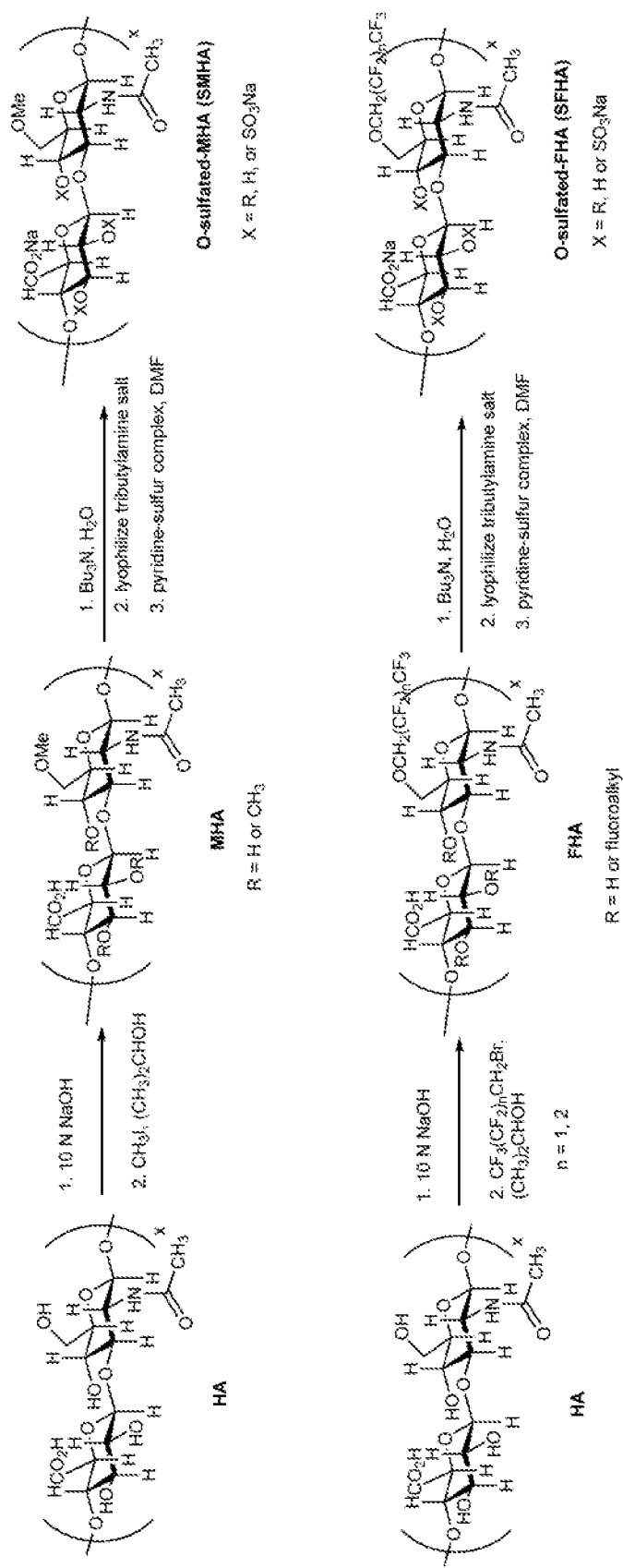
FIG. 1 shows a synthetic scheme for producing alkylated and fluoroalkylated hyaluronan and sulfated derivatives thereof.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y—OH, where Y is the remainder (i.e., residue) of the hyaluronan molecule.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "inhibit" as used herein is the ability of the compounds described herein to completely eliminate the activity or reduce the activity when compared to the same activity in the absence of the compound.

The term "urological inflammation" as used herein is defined as inflammation associated with any part or region of the genitourinary system. Urological inflammation includes, but is not limited to, inflammation of the bladder, urethra, urothelium lining, kidney, prostate, vagina, uterus, or any combination thereof.

The term "SAGE" as used herein is defined as an alkylated and fluoroalkylated semi-synthetic glycosaminoglycosan ether.

Described herein are methods for treating or preventing urological inflammation. In one aspect, the method involves administering to a subject a modified hyaluronan or a pharmaceutically acceptable salt or ester thereof, wherein said hyaluronan or its pharmaceutically acceptable salt or ester comprises at least one sulfate group and at least one primary C-6 hydroxyl position of an N-acetyl-glucosamine residue comprising an alkyl group or fluoroalkyl group.

In one aspect, at least one primary C-6 hydroxyl proton of the N-acetyl-glucosamine residue of the modified hyaluronan is substituted with an unsubstituted alkyl group. The term "alkyl group" as used herein is a branched or unbranched saturated hydrocarbon group of 1 to 24 carbon atoms. In one aspect, the alkyl group is a $C_1$-$C_{10}$ branched or straight chain alkyl group. The alkyl group can be unsubstituted or substituted. In the case when the alkyl group is substituted, one or more hydrogen atoms present on the alkyl group can be replaced with or more groups including, but not limited to, alkynyl, alkenyl, aryl, halide, nitro, amino, ester, ketone, aldehyde, hydroxy, carboxylic acid, aralkyl, or alkoxy. The term "unsubstituted" with respect to the alkyl group is a saturated hydrocarbon composed only of hydrogen and carbon. Examples of unsubstituted alkyl groups include, but are not limited to, methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like.

In another aspect, at least one primary C-6 hydroxyl proton of the N-acetyl-glucosamine residue of hyaluronan is substituted with a fluoroalkyl group. The term "fluoroalkyl group" as used herein is a branched or unbranched saturated hydrocarbon group of 1 to 24 carbon atoms, wherein at least one of the hydrogen atoms is substituted with fluorine. In certain aspects, the fluoroalkyl group includes at least one trifluoromethyl group. In other aspects, the fluoroalkyl group has the formula —$CH_2(CF_2)_nCF_3$, wherein n is an integer of 1, 2, 3, 4, 5, 6, 7, 8, 9, or 10. In one aspect, the fluoroalkyl group is —$CH_2CF_2CF_3$ or —$CH_2CF_2CF_2CF_3$.

In one aspect, the SAGEs are produced by (a) reacting the hyaluronan or a derivative thereof with a sufficient amount of base to deprotonate at least one primary C-6 hydroxyl proton of the N-acetyl-glucosamine residue, and (b) reacting the deprotonated hyaluronan or a derivative thereof with an alkylating agent or fluoroalkylating for a sufficient time and concentration to alkylate or fluoroalkylate at least one deprotonated primary C-6 hydroxyl group. It will be understood by those skilled in the art that the basic conditions may also lead to cleavage of the glycosidic linkage, leading to lower molecular weight hyaluronan derivatives during the modification process. It will also be understood that the basic conditions deprotonate the acid to the carboxylate, and the secondary hydroxyl groups, and that each of these nucleophilic moieties may participate in the ensuing alkylation in proportion to their relative abundance at equilibrium and the nucleophilicity of the anionic species. For example, 2-O and/or 3-O hydroxyl protons of the glucuronic acid moiety or the C-4 hydroxyl position of the N-acetyl glucosamine moiety can be deprotonated and alkylated or fluoroalkylated. An example of this is depicted in FIG. 1, where R can be hydrogen, an alkyl group, or an alkyl group. The hyaluronan starting material can exist as the free acid or the salt thereof.

Derivatives of hyaluronan starting material can also be used herein. The derivatives include any modification of the hyaluronan prior to the alkylation or fluoroalkylation step. A wide variety of molecular weight hyaluronan can be used herein. In one aspect, the hyaluronan has a molecular weight lower than 10 kDa prior to modification (i.e., alkylation, fluoroalkylation, and sulfation). In another aspect, the hyaluronan has a molecular weight from 10 kDa to 2,000 kDa, 25 kDa to 1,000 kDa, or 50 kDa to 500 kDa prior to alkylation or fluoroalkylation. In certain aspects, the hyaluronan starting material or a derivative thereof is not derived from an animal source. In these aspects, the hyaluronan can be derived from other sources such as bacteria. For example, a recombinant *B. subtilis* expression system or *Streptomyces* strain can be used to produce the hyaluronan starting material.

The hyaluronan starting material or derivative thereof is initially reacted with a sufficient amount of base to deprotonate at least one primary C-6 hydroxyl proton of the N-acetyl-glucosamine residue. The selection of the base can vary. For example, an alkali hydroxide such as sodium hydroxide or potassium hydroxide can be used herein. The concentration or amount of base can vary depending upon the desired degree of alkylation or fluoroalkylation. In one aspect, the amount of base is sufficient to deprotonate at least 0.001% of the primary C-6 hydroxyl protons of the N-acetyl-glucosamine residue of the hyaluronan starting material or derivative thereof. In other aspects, the amount of base is sufficient to deprotonate from 0.001% to 100%, 0.001% to 90%, 0.001% to 80%, 0.001% to 70%, 0.001% to 60%, 0.001% to 50%, 1% to 50% 5% to 45%, 5% to 40%, 5% to 30%, 5% to 20%, 10% to 50%, 20% to 50%, or 30% to 50% of the primary C-6 hydroxyl protons of the N-acetyl-glucosamine residue of the hyaluronan starting material or derivative thereof. It is understood that the more basic the solution, the more likely are chain cleavage reactions and the higher the degree of alkylation/fluoroalkylation that can be achieved. For example, other hydroxyl groups present on hyaluronan (e.g., 2-OH and/or 3-OH can be alkylated or fluoroalkylated). In one aspect, all of the hydroxyl groups present on hyaluronan can be alkylated or fluoroalkylated. In other aspects, 0.001%, 0.01%, 0.1%, 1%, 5%, 10%, 20%, 30%, 40%, 50%, 60%, 70%, 80%, 90%, 95%, 100%, or any range thereof of hydroxyl protons present on hyaluronan can be deprotonated and subsequently alkylated or fluoroalkylated.

After the hyaluronan starting material or derivative thereof has been treated with a base, the deprotonated hyaluronan is reacted with an alkylating agent or fluoroalkylating agent to produce the SAGE. Examples of alkylating agents include, but are not limited to, an alkyl halide. Alkyl bromides and iodides are particularly useful. Similarly, the fluoroalkylating agent can include a fluoroalkyl halide. Alkylating agents and fluoroalkylating agents commonly used in organic synthesis can be used herein.

An exemplary synthetic procedure for making alkylated and fluoroalkylated SAGEs is provided in FIG. 1. Referring to FIG. 1, hyaluronan (HA) is treated with a base (e.g., NaOH) and an alkylating agent (e.g., $CH_3I$) to methylate a primary C-6 hydroxyl proton of the N-acetyl-glucosamine residue of hyaluronan and produce methylated hyaluronan (MHA). FIG. 1 also provides an exemplary synthetic procedure for making a fluoroalkylated hyaluronan (FHA) using a fluoroalkylating agent (e.g., $CF_3(CF_2)_2CH_2Br$).

The alkylated or fluoroalkylated SAGE is sulfated by reacting the alkylated or fluoroalkylated SAGE with a sulfating agent to produce a sulfated product. The degree of sulfation can vary from partial sulfation to complete sulfation. In general, free hydroxyl groups present on the alkylated or fluoroalkylated hyaluronan or a derivative thereof can be sulfated. In one aspect, at least one C-2 hydroxyl proton and/or C-3 hydroxyl proton is substituted with a sulfate group. An additional embodiment can comprise a sulfate at the C-4 hydroxyl position of the N-acetyl glucosamine moiety or any combination of sulfation at the C-2, C-3 positions of the glucuronic acid moiety and C-4 hydroxyl position of the N-acetyl glucosamine moiety of the compound. The degree of sulfation can be from 0.5, 1.0, 1.5, 2.0, 2.5, 3.0, 3.5. 4.0, or any range thereof per disaccharide unit of the alkylated or fluoroalkylated SAGE. In one aspect, the alkylated or fluoroalkylated SAGE can be treated with a base to deprotonate one or more hydroxyl protons followed by the addition of the sulfating agent. The sulfating agent is any compound that reacts with a hydroxyl group or deprotonated hydroxyl group to produce a sulfate group. The molecular weight of the SAGE can vary depending upon reaction conditions. In one aspect, the molecular weight of the SAGE is from 2 kDa to 500 kDa, 2 kDa to 250 kDa, 2 kDa to 100 kDa, 2 kDa to 50 kDa, 2 kDa to 25 kDa, or from 2 kDa to 10 kDa. FIG. 1 depicts an exemplary synthesis of sulfated alkylated or fluoroalkylated SAGEs (SMHA and SFHA, respectively).

In one aspect, the alkyl group of the modified hyaluronan is methyl and at least one C-2 hydroxyl proton and/or C-3 hydroxyl proton of hyaluronan is substituted with a sulfate group. In another aspect, the alkyl group of the modified hyaluronan is methyl, at least one C-2 hydroxyl proton and/or C-3 hydroxyl proton of hyaluronan is substituted with a sulfate group, and the compound has a molecular weight of 2 kDa to 200 kDa after alkylation. An example of such a compound is GM-111101 as described in the Examples. An additional embodiment can comprise a sulfate at the C-4 hydroxyl position of the N-acetyl glucosamine moiety or any combination of sulfation at the C-2, C-3 positions of the glucuronic acid moiety and C-4 hydroxyl position of the N-acetyl glucosamine moiety of the compound. In certain aspects, when the C-6 position is not alkylated or fluoroalkylated, one or more C-6 positions are sulfated. In one aspect, up to 50%, up to 60%, up to 70%, up to 80%, up to 90%, up to 95%, or 100% of the C-6 positions are sulfated. In other aspects, all of the C-6 positions are modified, either by alkylation and/or fluoroalkylation or by sulfation.

The modified hyaluronans described herein can be prepared from different sources of hyaluronic acid with different polydispersities and initial average molecular weights. The in vitro biochemical results, in vivo biological activities, and alkylation/sulfation levels can vary based on the size and solubility of the starting HA. For example, starting with readily soluble HA of sizes 5-60 kDa resulted in reproducible levels of methylation, sulfation, and high biological activity.

In one aspect, a partially or fully sulfated hyaluronan or the pharmaceutically acceptable salt or ester thereof can be administered to a subject in order to treat or prevent urological inflammation. The term "partially sulfated hyaluronan" as used herein is when the hyaluronan has a degree of sulfation less than 3.5 per disaccharide unit. The term "fully sulfated hyaluronan" as used herein is when the hyaluronan has a degree of sulfation of 3.5 to 4.0 per disaccharide unit. In this case, the majority if not all of the hyaluronan C-6 hydroxyl groups are sulfated.

The hyaluronan starting material can exist as the free acid or the salt thereof. Derivatives of hyaluronan starting material can also be used herein. The derivatives include any modification of the hyaluronan prior to sulfation. A wide variety of molecular weight hyaluronans can be used herein for the depolymerization step. In one aspect, the hyaluronan has a molecular weight greater than 1,000 kDa prior to depolymerization. In another aspect, the hyaluronan can have a molecular weight of 10 kDa to 1,000 kDa prior to depolymerization. In another aspect, the hyaluronan can have a molecular weight of less than 10 kDa prior to depolymerization. A wide variety of hyaluronan molecular weights can also be employed for the sulfation step. In one aspect, the hyaluronan starting material can be converted to low molecular hyaluronan or a hyaluronan oligosaccharide prior to sulfation to produce the partially sulfated hyaluronan. As will be discussed in greater detail below, low molecular weight hyaluronan is hyaluronan that has been degraded with an acid or base. Alternatively, hyaluronan oligosaccharide is produced by degrading hyaluronan with an enzyme such as, for example, hyaluronan synthase or hyaluronidase in a controlled fashion. Subsequently, hyaluronan oligosaccharides having different molecular weights can be separated by GPC or ion exchange separation. FIG. 1 depicts exemplary procedures for producing low molecular hyaluronan or hyaluronan oligosaccharide from hyaluronan.

In one aspect, the hyaluronan or hyaluronan oligosaccharide being sulfated has a molecular weight from 1 kDa to 2,000 kDa. In another aspect, the low molecular hyaluronan or hyaluronan oligosaccharide being sulfated has a molecular weight from 5 kDa to 500 kDa, 10 kDa to 200 kDa, or 20 kDa to 100 kDa. Exemplary procedures for preparing low molecular weight hyaluronan are provided in the Examples. As discussed above, the molecular weight of the hyaluronan can be modified by cleaving hyaluronan with an acid or base to produce lower molecular weight hyaluronan. In certain aspects, the hyaluronan starting material or a derivative thereof is not derived from an animal source. In these aspects, the hyaluronan can be derived from other sources such as bacteria. For example, a recombinant B. subtilis expression system can be used to produce the hyaluronan starting material.

Figure 2:
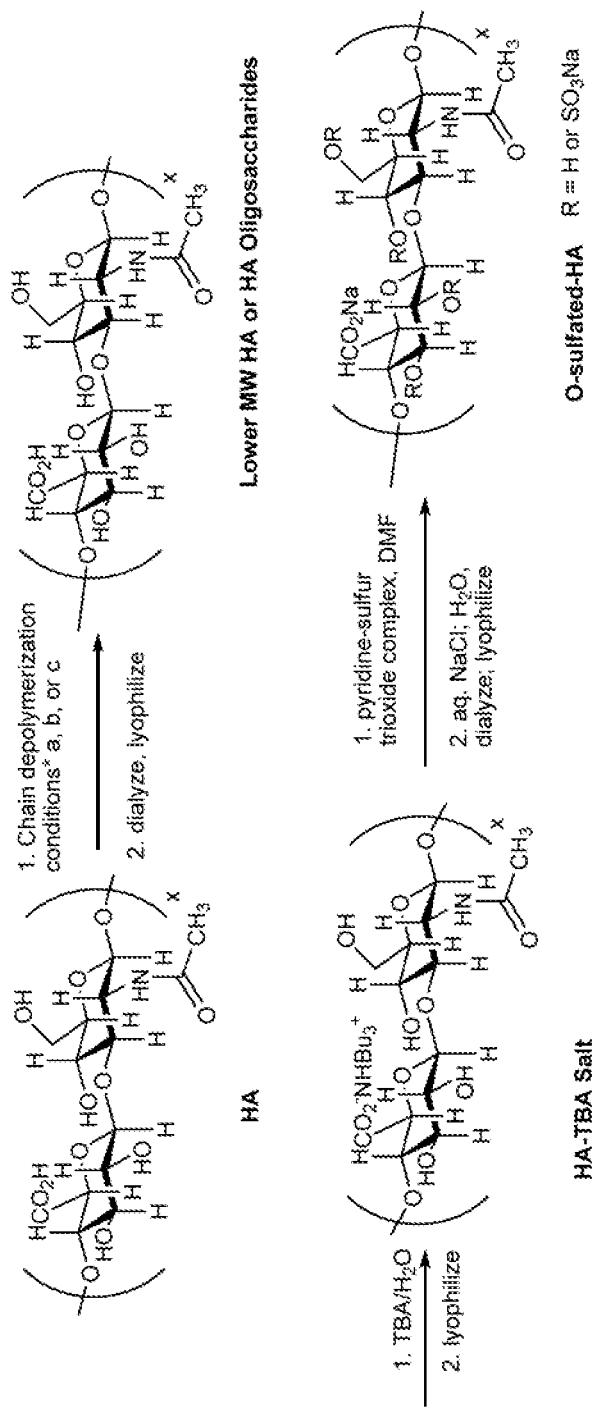
FIG. 2 shows an exemplary synthetic procedure for making partially sulfated hyaluronan by (1) partial depolymerization by controlled hydrolytic chain cleavage, (2) conversion to a tributylammonium salt, and (3) sulfation to produce the partially sulfated hyaluronan.

After the low molecular hyaluronan or hyaluronan oligosaccharide has been treated with a base, it is reacted with a sulfating agent to produce the partially or fully sulfated hyaluronan. Sulfating agents commonly used in organic synthesis can be used herein. Examples of sulfating agents include, but are not limited to, pyridine-sulfur trioxide complex, triethylamine-sulfur trioxide complex, or dimethyl formamide-sulfur trioxide complex. An exemplary synthetic procedure for making partially sulfated hyaluronan is provided in FIG. 2. Referring to FIG. 2, low molecular hyaluronan or hyaluronan oligosaccharide is converted to the tributylamine salt, lyophilized, resuspended in dimethylformamide, and subsequently treated with a sulfating agent (e.g., pyridine-sulfur trioxide complex, triethylamine-sulfur trioxide complex, or dimethyl formamide-sulfur trioxide complex) to sulfate one or more hydroxyl protons. It is known in the art that in some cases, sulfation of polysaccharides with pyridine-sulfur trioxide complex can result in partial strand scission of the polysaccharide, creating a reducing end that can be converted to a glycosyl sulfate and react with the pyridine in the complex, forming and N-glycosyl-pyridinium complex of the polysaccharide fragment. In some aspects these complexes show loss of efficacy or detrimental effects. In other aspects, the complexes of sulfated HA have surprisingly been found to both retain activity or even show improved activity.

In one aspect, the degree of sulfation is from 0.1, 1.0, 1.5, 2.0, 2.5, 3.0, 3.5, or up to 4.0 or any range thereof per disaccharide unit of the partially sulfated hyaluronan. In another aspect, the partially sulfated hyaluronan has a degree of sulfation of about 2.5 up to 4.0, 2.5 to 3.5, or 3.0 to 3.5. In one aspect, the average molecular weight of the partially or fully sulfated hyaluronan is less than 100 kDa. In another aspect, the partially or fully sulfated hyaluronan has an average molecular size from 1 kDa to less than 50 kDa, 2 Da to 20 kDa, or 3 kDa to 10 kDa. In one aspect, the partially or fully sulfated hyaluronan has an average molecular size of about 3 kDa, 4 kDa, 5 kDa, 6 kDa, 7 kDa, 8 kDa, 9 kDa, or 10 kDa, where any value can form a lower or upper end-point of a range. In another aspect, the partially or fully sulfated hyaluronan has an average molecular size of about 3 kDa to less than 10 kDa, about 3 kDa to about 9 kDa, about 3 kDa to about 8 kDa, about 3 kDa to about 7 kDa, about 3 kDa to about 6 kDa, about 4 kDa to about 6 kDa, or about 5 Kda. Depending upon reaction conditions, one or more different hydroxyl groups present in the low molecular hyaluronan or hyaluronan oligosaccharide can be sulfated. In one aspect, the primary C-6 hydroxyl proton of the N-acetyl-glucosamine residue of the low molecular hyaluronan or hyaluronan oligosaccharide is sulfated. In another aspect, the primary C-6 hydroxyl proton of the N-acetyl-glucosamine residue of hyaluronan and at least one C-2 hydroxyl proton or C-3 hydroxyl proton of a uronic acid residue or at least one C-4 hydroxyl proton of an N-acetyl-glucosamine residue is substituted with a sulfate group. In another aspect, the primary C-6 hydroxyl proton of the N-acetyl-glucosamine residue of the low molecular hyaluronan or hyaluronan oligosaccharide and at least one C-2 hydroxyl proton and C-3 hydroxyl proton of a uronic acid residue and at least one C-4 hydroxyl proton of an N-acetyl-glucosamine residue is substituted with a sulfate group. In another aspect, 0.001%, 0.01%, 0.1%, 1%, 5%, 10%, 20%, 30%, 40%, 50%, 60%, 70%, 80%, 90%, 95%, or less than 100%, or any range thereof of hydroxyl protons present on the low molecular hyaluronan or hyaluronan oligosaccharide can be deprotonated and subsequently sulfated.

The modified hyaluronan or partially/fully sulfated hyaluronan described herein can be the pharmaceutically acceptable salt or ester thereof. Pharmaceutically acceptable salts are prepared by treating the free acid with an appropriate amount of a pharmaceutically acceptable base. The pharmaceutically acceptable salt can be an organic salt, a metal salt, or a combination thereof. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, 2-trimethylethanolammonium cation (choline), lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds, as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine. Also, the esters can be fatty acid esters. For example, the palmitic ester has been prepared and can be used as an alternative esterase-activated prodrug.

The modified hyaluronan or partially/fully sulfated hyaluronan described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the compounds described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds.

Examples of such compounds include, but are not limited to, antimicrobial agents, antiinflammatory agents, anesthetics, and the like. Methods for using these compositions as drug delivery devices are described in detail below.

The pharmaceutical compositions can be prepared using techniques known in the art. In one aspect, the composition is prepared by admixing the modified hyaluronan or partially/fully sulfated hyaluronan described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible. Third, electrostatic or hydrophobic interactions can facilitate retention of a pharmaceutically-acceptable compound in the compounds described herein.

It will be appreciated that the actual preferred amounts of the modified hyaluronan or partially/fully sulfated hyaluronan in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The pharmaceutical compositions described herein can be administered in a number of ways depending on whether local or systemic treatment is desired, and on the area to be treated. Formulations can include ointments, lotions, creams, gels, drops, suppositories, sprays, lozenges, liquids and powders. Conventional pharmaceutical carriers, aqueous, powder or oily bases, thickeners and the like can be necessary or desirable. Administration can also be directly into the lung by inhalation of an aerosol or dry micronized powder. Administration can also be by direct injection into the inflamed or degenerating joint space. Administration can also occur intravenously, intramuscularly, subcutaneously, by ingestion, or transmuco sally. Transmucosal routes may include transbuccal, sublingual, oral, vaginal, intranasal, rectal, and the like. Administration can also occur by intravesical instillation, i.e., via urethral catheter into the bladder.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

The modified hyaluronan or partially/fully sulfated hyaluronan can be injected parenterally, either intravenously, intramuscularly or subcutaneously, to treat or prevent systemic urological inflammatory disorders. Similarly, the modified hyaluronan or partially/fully sulfated hyaluronan can also be administered orally in capsules, in tablets, in chewing gum, in lozenges, in powders, or in a beverage. Alternatively, the modified hyaluronan or partially/fully sulfated hyaluronan can be administered by intravesical installation (i.e., via a catheter).

The modified hyaluronan or partially/fully sulfated hyaluronan described herein can deliver at least one pharmaceutically-acceptable compound to a patient in need of such delivery, comprising contacting at least one tissue capable of receiving the pharmaceutically-acceptable compound with one or more compositions described herein. The modified hyaluronan or partially/fully sulfated hyaluronan can be used as a carrier for a wide variety of releasable biologically active substances having curative or therapeutic value for human or non-human animals. Many of these substances that can be carried by the modified hyaluronan or partially/fully sulfated hyaluronan are discussed above. Included among biologically active materials which are suitable for incorporation into the gels of the invention are therapeutic drugs, e.g., anti-inflammatory agents, antipyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathimometic agents, cardiovascular agents, antitumor agents, oligonucleotides and their analogues and so forth. A biologically active substance is added in pharmaceutically active amounts.

The modified hyaluronan or partially/fully sulfated hyaluronan described herein are safer than other related therapies. For example, heparin and other sulfated polysaccharides can reduce diabetic complications in both animal and clinical studies, and are particularly effective against diabetic nephropathy. However, heparins cannot be used in general clinical settings to prevent diabetic complications because the anticoagulant properties present an excessive risk of bleeding. The modified hyaluronan or partially/fully sulfated hyaluronan described herein possess low anticoagulant activity, which is an important consideration for long-term treatment, which is demonstrated below in the Examples. Additionally, the SAGEs have little to no toxicity, which is also demonstrated in the Examples.

In one aspect, the modified hyaluronan or partially/fully sulfated hyaluronan described herein can inhibit the activity of LL-37 in a subject. LL-37 is a host defense peptide produced from the C-terminus of the hCAP18 precursor protein and is produced in circulating neutrophils, cells of the mucosal epithelium, keratinocytes, myeloid bone marrow cells, epithelial cells of the skin, gastrointestinal tract, epididymis gland and lungs. LL-37 is produced by epithelial cells (urothelial cells) of the urinary tract in both humans and mice, with significantly elevated urinary levels during episodes of kidney and/or bladder infections (pyelonephritis or cystitis). In addition to the role that LL-37 has in eradicating microbes, it is immunomodulatory and triggers inflammation via the promotion of leukocyte chemotaxis, angiogenesis, stimulating mast cell degranulation, enhancing neutrophil function, inducing chemokines including IL-8, regulating inflammatory responses via NF-κB, and increasing expression of extracellular matrix components. While the details of the downstream inflammatory mechanisms of action for LL-37 are not completely understood, responses involve the activation of a number of cell-surface receptors and signaling pathways. As shown in the Examples, the inhibition of LL-37 by compounds described herein not only is useful in treating urological inflammation but can also be useful in preventing urological inflammation.

Based on the link between elevated levels of LL-37 and the occurrence of urological inflammation, described herein is a method for screening a compound's ability to treat or prevent urological inflammation in a subject. In one aspect, the method involves:

administering to a laboratory animal an amount of LL-37 that induces inflammation in the subject;

administering to the animal prior to step (a) and/or after step (a) the compound; and comparing the amount of inflammation in the animal to a control animal that was administered the same amount of LL-37 but not the compound.

In one aspect, a murine model can be used to screen the ability of different compounds to inhibit LL-37 and, thus, treat or prevent urological inflammation. Exemplary procedures for screening compounds useful in the treatment and prevention of urological inflammation are provided in the Examples.

In certain aspects, it is desirable to track the ability of the modified hyaluronan or partially/fully sulfated hyaluronan to penetrate and localize in a urological tissue. For example, the modified hyaluronan or partially/fully sulfated hyaluronan can be fluorescently labeled. In one aspect, the fluorescently labeled modified hyaluronan or a pharmaceutically acceptable salt or ester thereof, comprises (a) at least one sulfate group; (b) at least one primary C-6 hydroxyl position of an N-acetyl-glucosamine residue comprising an alkyl group or fluoroalkyl group, and (c) a fluorescent group covalently bonded to at least one disaccharide unit. Exemplary procedures for making the fluorescently labeled modified hyaluronan are provided in the Examples.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Evaluation of Alkylated and Sulfated Hyaluronan
Preparation of GM-1111

The modified hyaluronan GM-1111 evaluated in the studies below was previously synthesized in International Publication No. WO 2009/124266, which is incorporated by reference. The structure of GM-1111 is provided in FIG. 1, and is shown as "SMHA").

LL-37 Induced Model of Bladder Inflammation

All animal experiments were performed under full approval and in accordance with the Institutional Animal Care and Use Committee at the University of Utah. Adult female C57/B16 mice (Charles River, Wilmington, Mass.), 8 to 12 weeks old, were utilized for all animal experiments. All animals were housed and maintained in a pathogen-free environment, received food and water ad libitum with a 12 h light cycle. Synthesized LL-37 was purchased in HPLC-homogenous form from the University of Utah Core Facility (peptide sequence: LLGDFFRKSKEKIG-KEFKRIVQRIKDFLRNLVPRTES), and dissolved in nanopure water to give a working concentration of 320 μM. Each experimental group consisted of 6 mice. Following isoflurane (Minrad, Bethlehem, Pa.) mediated general anesthesia, a flexible catheter (SILASTIC laboratory tubing, DOW Corning, 0.30 mm I.D.×0.64 mm O.D., 1.5 cm length) was introduced under sterile conditions transurethrally. After complete drainage of urine, 150 μl of pyrogen-free 0.9% sodium chloride solution was instilled for 1 min and emptied as a washing step. Next, LL-37 (320 μM) was instilled at a volume equal to maximum capacity (150 μl) with an intravesical contact/dwell time of 45 min. Controls consisted of pyrogen-free 0.9% sodium chloride instillation, at the same volume and contact/dwell time as the experimental group. To avoid possible injury to the bladder from abrupt over distension, and prevention of potential vesicoureteral reflux, infusion manipulation was kept at a slow velocity and the instillation syringe was kept on the catheter to assure no leakage of solution occurred during the entire 45 min period. After the 45 min contact/dwell time, bladders were then emptied to completion and animals allowed to arise from anesthesia. Depending on the experimental group, animals were sacrificed and tissues harvested at either 12 or 24 h following the intravesical administration.

Modified Hyaluronan and Heparin Treatment of LL-37 Induced Bladder Inflammation

Two experimental groups were examined for both SAGE and heparin treatment. Mice were anesthetized and catheterized as detailed previously. Group 1 (n=4 for each SAGE and heparin treatment) consisted of first instilling LL-37 (320 μM) at maximum bladder capacity (150 μl) for 45 min, then emptied to completion. Immediately thereafter, either SAGE or heparin at 10 mg/ml was instilled at maximum bladder capacity (150 μl) for 45 min. Bladders were then harvested at 24 h following SAGE or heparin intravesical administration. Group 2 (n=4 for each SAGE and heparin treatment) consisted of first instilling SAGE or heparin at 10 mg/ml at maximum bladder capacity for 45 min. Bladders were then emptied and challenged with LL-37 (320 μM) for 45 min. Tissues were then harvested at 24 h following LL-37 administration. All bladder tissues were hemisected, processed, fixed, and either H&E stained or tissue MPO assays performed to quantitate levels of inflammation.

Synthesis of Fluorescent GM-1111

To a stirred solution of 50 mg of the GM-1111 (Table 1) and 10 mg of N-hydroxysuccinimide (NHS) in 10 mL of deionized (DI) $H_2O$ was added a solution of 1 mg of AlexaFluor 633 hydrazide (Invitrogen, Eugene, Oreg.) in 4 mL of dimethylformamide (DMF). The pH was adjusted to 4.75, and 10 mg of powdered N,N-diethylaminopropyl carbodiimide (EDCI) was added. The pH of mixture was maintained at 4.75 by dropwise addition of 3 N NaOH. The reaction mixture was protected from light with Al foil, and stirred overnight at room temperature. The reaction mixture was then dialyzed twice against 100 mM NaCl solution (MWCO 1000), and then once against DI $H_2O$. The dialyzed solution was lyophilized to dryness to give 25 mg of the GM-1111-Alexa Fluor 633 conjugate. The substitution degree (SD) was determined from absorption of a 1 mg/mL solution at 632 nm using a Cary 50 UV-Vis spectrophotometer, Varian, Inc., Palo Alto, Calif.). For GM-1111 with an average MW of 5000 Da and disaccharide weight of 539 (nine disaccharides) and 1200 Da for AlexaFluor 633, the SD was 14%, or approximately one AlexaFluor 633 modification per seven disaccharide units.

Coating of Bladders by Instillation of AlexaFluor 633-GM-1111

Mice were anesthetized and catheterized in the same fashion as detailed above. Bladders were instilled with the SAGE AlexaFluor 633 bioconjugate (10 mg/ml) at maximum bladder capacity (150 μl) for 45 min. Bladders were then harvested immediately thereafter (t=0) or after 24 h (t=24) of intravesical SAGE administration. All tissues were processed, fixed and sectioned under light sensitive conditions. Tissue sections were counterstained with DAPi in order to identify all cellular nuclei. Fluorescence imaging was carried out at the University of Utah CORE facilities utilizing a FV1000 Confocal Olympus IX81 microscope and HeNe laser with variable emission filters.

Tissue Collection and Histological Evaluation

Bladders were removed and split longitudinally. One section of the bladder was fixed in 4% paraformaldehyde, and the second section was processed for tissue myeloperoxidase (MPO) assay. Gross images of hemi-sected bladders were performed with a dissecting stereo microscope and photographed with a Moticam 1000 digital camera (Moticam North America, Richmond, Calif.). To assess inflammatory changes in bladders, tissues were processed through a graded alcohol series and embedded in paraffin, and 5 μM sections were cut and stained with hematoxylin and eosin (H&E). Severity of bladder inflammation was assessed by the presence and degree of inflammatory infiltrate (polymorphonuclear leukocytes (PMNs)) in the bladder epithelium (urothelium), submucosa, lamina propria and smooth muscle layers, the presence and extent of edema and hemorrhage, and the presence of surface urothelial changes, including erosion, ulceration, and microabscess formation. Individual slides were examined and photographed on an Olympus BX41 microscope (Olympus Corporation, Tokyo, Japan) and an Imaging Planet 1.4 MPX digital microscope camera (Imaging Planet Research, Goleta, Calif.).

Tissue Myeloperoxidase Assay

Hemi-sected bladders destined for tissue MPO assays were flash frozen in liquid nitrogen and stored in −80° C. Lysis buffer (200 mM NaCl, 5 mM EDTA, 10 mM Tris, 10% glycerin) (SIGMA, St. Louis, Mo.), and protease inhibitor cocktail (Thermo Scientific, Cat #78140, Rockford, Ill.) were added to frozen tissue samples (200 µl lysis buffer/10 mg frozen tissue). Tissues were then minced with micro-scissors and homogenized for 90 seconds at 4° C. with a small sample lab Tissue-Tearor Homogenizer (Biospec Products, Model #985-370, Bartlesville, Okla.). Samples were centrifuged twice for 15 min each (1500 g at 4° C.) and supernatant was transferred to new sterile tubes. The activity of MPO was quantified in bladder sample homogenates using an MPO Sandwich ELISA Kit (Cell Sciences, Cat #HK210, Canton, Mass.). Briefly, samples were diluted 1:5 with ELISA kit Diluent Buffer and assay was carried out following manufactures recommendations. 100 µl duplicates of standards, samples and controls were added to wells. Unless otherwise specified, all incubations were carried out at R.T. for one h, followed by washing. Tracer and streptavidin-peroxidase were added sequentially following incubation and washing procedures. TMB substrate was added and incubated for 25 min. Stop solution was then added and absorbance was measured at 450 nm in a microplate reader (Optimax Tunable, Molecular Devices, Sunnyvale, Calif.). A standard curve was generated on each sample plate, and a linear regression curve was generated. All values were expressed as means+/−SD.

Anti-Coagulant Properties and Toxicity

GM-1111 showed no anti-Xa and <0.2 U/mg anti-IIa anticoagulant activity, compared to 150 U/mg each for unfractionated heparin. Unlike heparin, highly-charged polyanionic polymers are potent inducers of the intrinsic coagulation cascade by activation of Factor XII, secondarily activating kinins. GM-1111 appears safer than medical heparin in tests for activation of Factor XII, even at concentrations 10-100-fold higher than needed to achieve pharmacologic inhibition of P-selectin and RAGE. GM-1111 appears to have optimal safety and broad efficacy.

GM-1111 showed no toxicity for cultured fibroblasts or epithelial cells and no cutaneous toxicity in standard Draize tests. In a preliminary non-GLP study on the effects of GM-1111 as a single i.v. dose to rats, and in daily i.v. injections (n=3 rats per sex), GM-1111 did not produce signs of toxicity at any dose level for single acute doses as high as 100 mg/kg and 7 repeated i.v. daily doses of 10 mg/kg. The i.v. $LD_{50}$ for GM-1111 is >100 mg/kg.

Results

LL-37 Induced Bladder Inflammation

Figure 3:
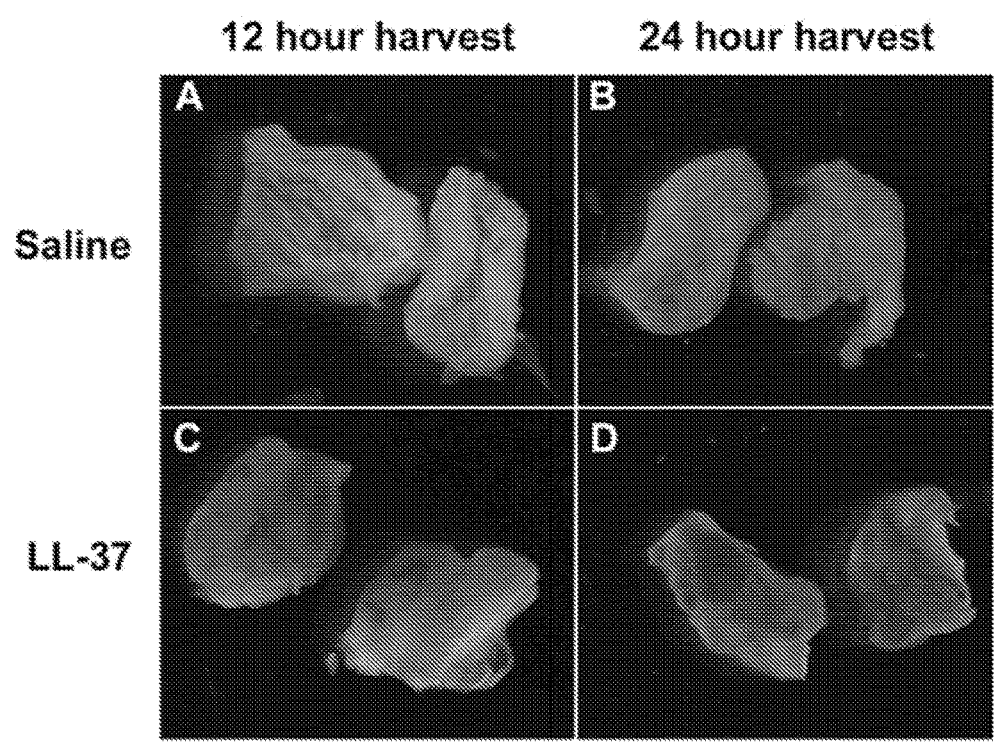
FIG. 3 shows gross bladder images comparing saline control versus LL-37 instilled bladders. Saline instilled control bladders harvested after 12 h (A) and 24 h (B). Hemisected bladders exposing inner mucosal layer, no evidence of inflammation. LL-37 instilled bladders (single 45 min instillation) harvested after 12 h (C) and 24 h (D). After 12 h (C), moderate inflammation observed, focal areas of erythema/hemorrhage, & global edema. After 24 h (D), severe inflammation observed, global erythema/hemorrhage, significant edema & hypervascularity apparent.

After one single intravesical exposure to LL-37, tissues were harvested and examined at 12 and 24 h. On gross inspection after 12 h, the bladders appeared to have moderate inflammation, characterized by focal areas of erythema and hemorrhage, along with global edema (FIG. 3C). After 24 h, the bladders appeared to have severe inflammation, characterized with global erythema and hemorrhage, along with significant tissue edema and hypervascularity (FIG. 3D). Saline exposed control tissues at both time points were completely normal, with no evidence of inflammation observed (FIGS. 3A & 3B).

Both 12 and 24 h tissues were then processed and evaluated by histology with H&E staining. As illustrated in FIGS. 3A & 3B, no inflammation was observed in the saline exposed controls as expected at both time points. The urothelium, submucosa, lamina propria, and smooth muscle layers were completely intact with no evidence of PMN or lymphocyte infiltration, and lack of tissue edema. In the LL-37 exposed tissues after 12 h (FIG. 3C), there were focal areas of urothelial cell ulceration and moderate tissue edema present in the submucosa and lamina propria layers. In addition, a moderate number of PMNs were observed within the urothelial, submucosa and lamina propria (superficial and deep) layers, along with PMNs marginating out of blood vessels. No evidence of microabscesses (PMN clusters) were observed after 12 h. The evidence from both the gross and histologic findings demonstrated that a moderate tissue inflammatory response had occurred after 12 h. These findings were consistently observed for all six mice in the 12 h harvest group.

Figure 4:
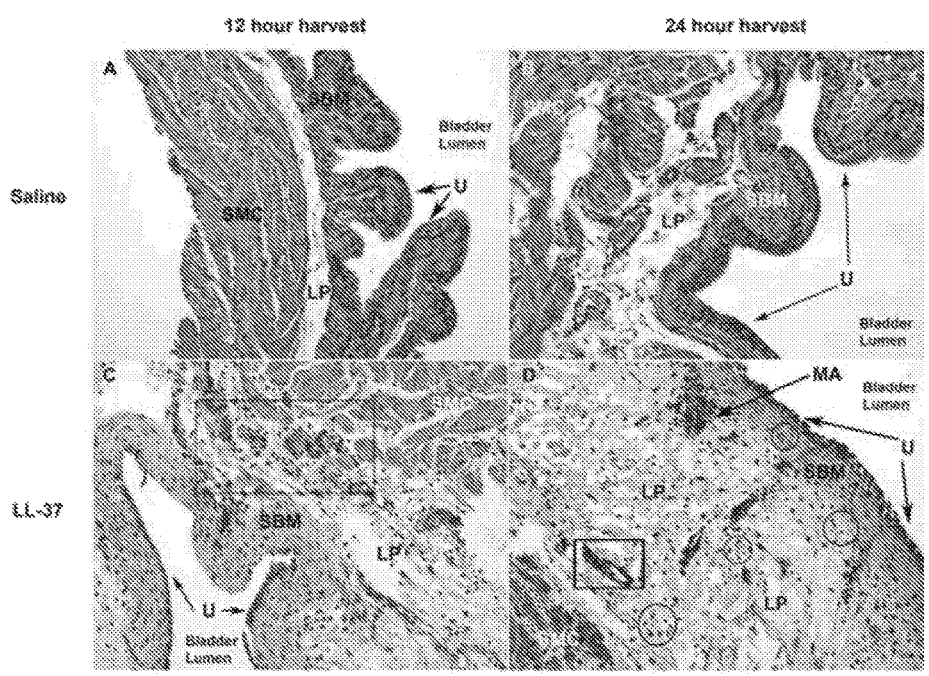
FIG. 4 shows H&E histology comparing saline control versus LL-37 instilled bladders. Saline instilled control bladders harvested after 12 h (A) and 24 h (B). Cross section histology demonstrated no evidence of inflammation at 12 or 24 h (U-urothelium, SBM-submucosa, LP-lamina propria, SMC-smooth muscle cell layer). LL-37 instilled bladders (single 45 min instillation) harvested after 12 h (C) and 24 h (D). After 12 h (C), moderate inflammation observed, focal areas of urothelial ulceration, moderate tissue edema in SBM and LP layers. Moderate PMN infiltration in all layers (U, SBM, LP, & SMC), along with PMN margination out of blood vessels (rectangle). No evidence of microabscess (MA) formation. After 24 h (D), severe inflammation observed, moderate edema in SBM, and severe edema in LP. Significant PMN infiltration in all layers (circles), MA formation, and PMN margination out of blood vessels (rectangle). All images at 10× magnification.

For the 24 h harvest group, the histological evaluation of the LL-37 exposed bladders yielded a similar inflammatory response, but more profound levels of inflammation were apparent (FIG. 4D). The qualitative amount of tissue edema present in the submucosa was similar between the 24 h and 12 h tissues, but the lamina propria did yield more profound levels of edema. In addition, the 24 h tissue did have significantly more PMNs present in the urothelial, submucosa, and lamina propria (superficial and deep) layers. Furthermore, the 24 h tissues had multiple areas with microabscesses (PMN clusters) present, further signifying a more profound inflammatory response. Similar patterns of PMN margination out of blood vessels were seen for both harvest groups. The evidence from both the gross and histologic findings for the 24 h harvest group demonstrated that severe levels of inflammation were apparent after one single LL-37 exposure, more so than for the 12 h harvest group. Similar to the 12 h harvest group, findings were consistently observed for all six mice in the 24 h cohort.

The degree of inflammation was quantified using a tissue MPO assay. MPO is glycoprotein expressed in all cells of the myeloid lineage and is abundantly present in azurophilic granules of PMNs. It is an important enzyme released by activated PMNs during episodes of infection or inflammation, and is therefore utilized as a quantitative marker for inflammation. Our results comparing the 12 h harvest tissues (FIG. 5) illustrated minimal MPO activity for control saline instilled bladders (11 ng/ml) and control non-manipulated/non-instilled bladders (5 ng/ml). Strikingly, the LL-37 exposed tissues after 12 h yielded a 21-fold increase in MPO activity (229 ng/ml) when compared to control saline exposed samples (11 ng/ml). Further evaluation of the 24 h harvest tissues (FIG. 5) again yielded minimal MPO activity in the control saline exposed tissues (14 ng/ml) versus a 61-fold increase (849 ng/ml) in the LL-37 exposed bladders. The MPO data support and are consistent with the H&E histology. Thus, moderate levels of inflammation were present after a 12 h period, with an increased level of inflammation after 24 h.

Modified Hyaluronan Abrogation of LL-37 Induced Bladder Inflammation

The ability of the GM-1111 to either prevent or mitigate LL-37 induced bladder inflammation was evaluated by instillation of a 10 mg/ml solution of the sulfated polysaccharide. Two groups were examined. Group 1 (post-treatment, n=4) consisted of LL-37 exposure for 45 min then followed by treatment with GM-1111 immediately thereafter (45 min dwell time). Group 2 (pre-treatment, n=4) consisted of treatment with GM-1111 (45 min dwell time) then followed with LL-37 exposure for 45 min. Group 2 served to evaluate if pre-coating would yield a prophylactic effect. In both groups, mice were sacrificed after 24 h and bladders were harvested, imaged, processed, and H&E stained.

Figure 6:
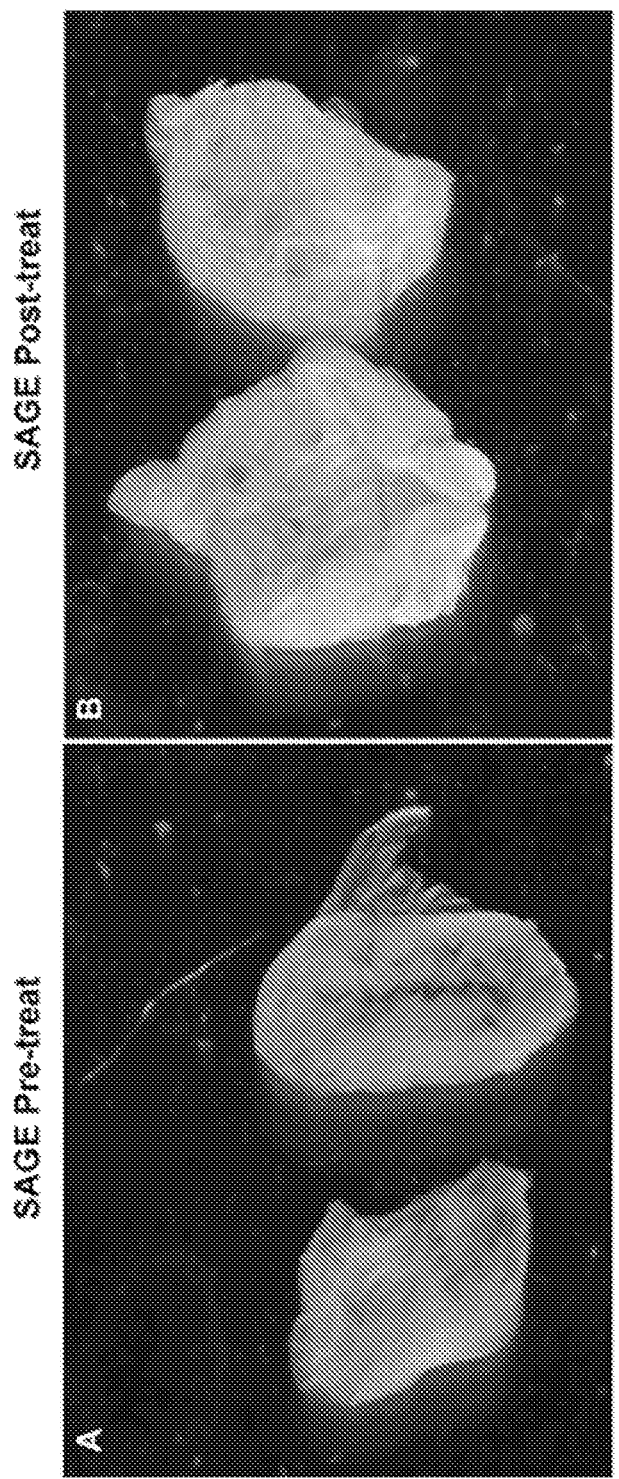
FIG. 6 shows Gross images (bladders hemisected exposing inner mucosal surface) of GM-1111 (10 mg/ml) pre-coat/treatment prior to LL-37 instillation (A) versus GM-1111 (10 mg/ml) post-treatment after LL-37 instillation (B). All tissues harvested after 24 h. Minimal inflammation observed in (A), only mild edema and patchy hypervascularity. Moderate inflammation observed in (B), moderate edema but no evidence of hemorrhage. Panels (C) & (D) tissue histology ((C) corresponds to (A), (D) corresponds to (B)). SAGE pre-coat/treatment (C) yielded mild edema in the submucosa (SBM) but no evidence of edema in the lamina propria (LP). No evidence of PMNs were observed throughout all layers, along with a lack of margination out of blood vessels. GM-1111 post-treatment (D) yielded edema present in the SBM and LP, but the urothelium and SBM had a complete lack of PMNs, along with significantly fewer PMNs in the LP layer. PMN's present (circles) (G) were more condensed in the deeper LP layer adjacent to the smooth muscle cell layer (SMC). No significant evidence for PMN margination out of blood vessels observed (rectangle). Panel (E) represents tissue MPO assay for GM-1111 pre-coat/treatment, illustrating a 22-fold reduction in MPO activity in pre-treated samples (purple bar). Panel (F) represents tissue MPO assay for GM-1111 post-treatment, illustrating a 2.5 fold reduction in MPO activity in post-treated samples (purple bar). All histology images at 10× magnification.
Figure 6:
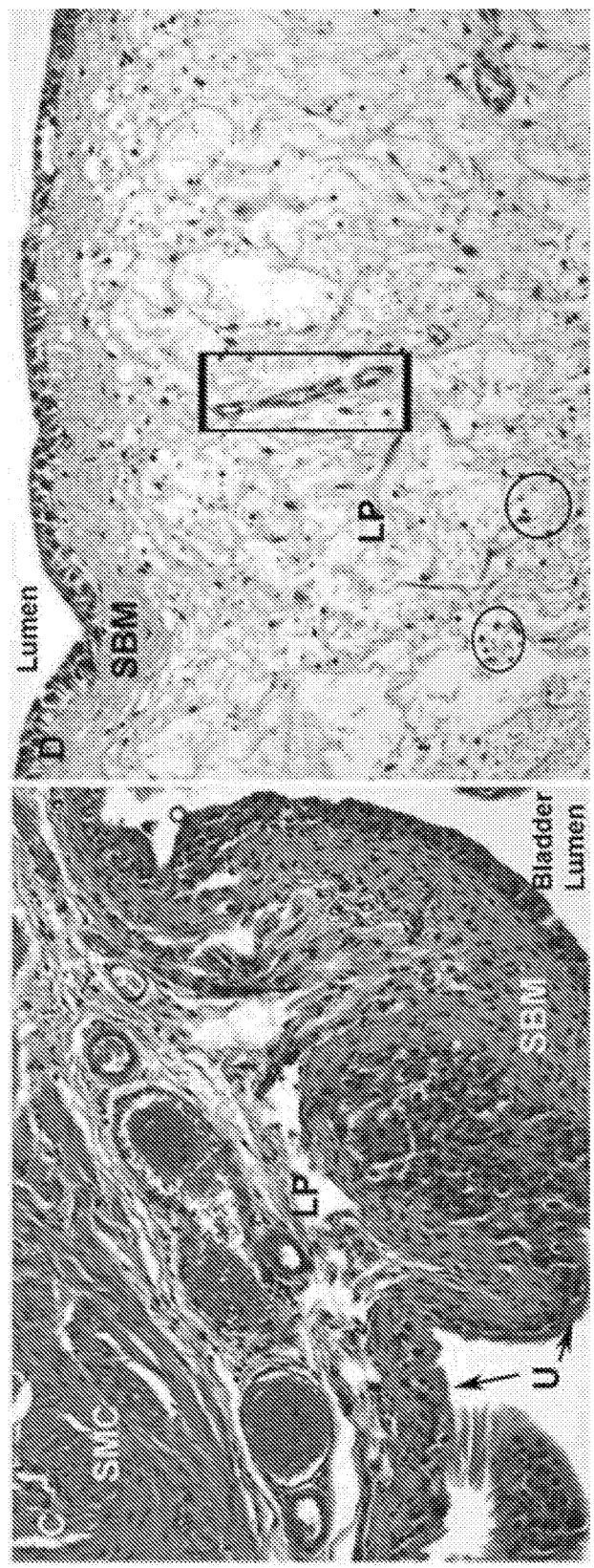
Figure 6:
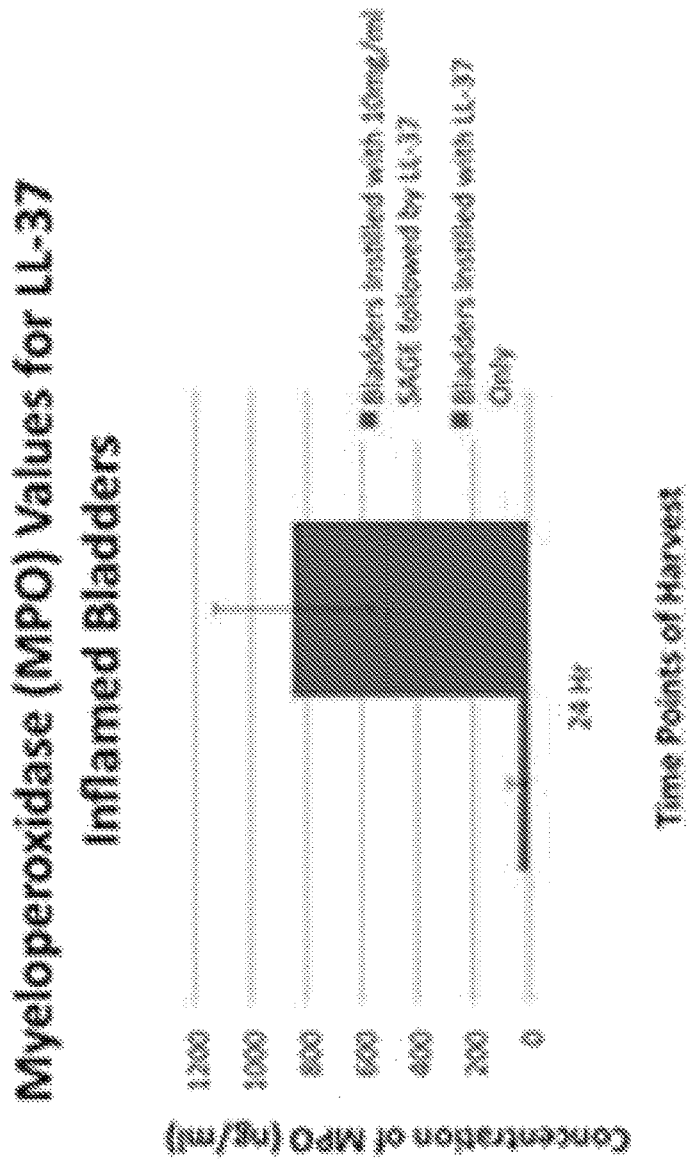
Figure 6:
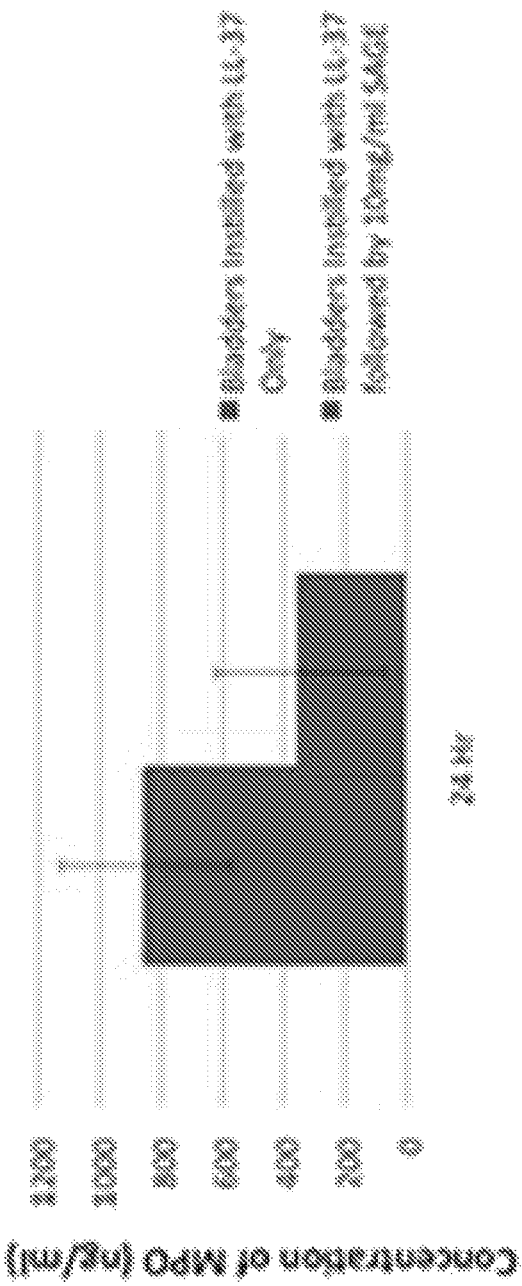

In group 1, gross inspection of the GM-1111 post-treated bladders appeared to show less erythema and hypervascularity, but bladders were still edematous (FIG. 6B). Histologic evaluation revealed edema in the submucosa and lamina propria, although strikingly the urothelium and submucosa had a complete lack of PMNs, along with significantly fewer PMNs seen throughout the lamina propria layer. In addition, the PMNs that were present appeared to be limited to the deeper lamina propria layer, a finding consistent with a gradient type of response (FIG. 6D). Furthermore, no evidence of microabscess formation was observed in the SAGE treated bladders, along with a paucity of PMNs rolling out of blood vessels. Inflammatory quantification with tissue MPO assay, comparing LL-37 inflamed bladders vs. group 1 tissues revealed a 2.5 fold diminished inflammatory response in GM-1111 treated bladders (FIG. 3F—blue bar) (LL-37 MPO activity 849 ng/ml vs. group 1 post-treatment with SAGE MPO activity 347 ng/ml).

In group 2, gross inspection yielded SAGE pre-treated bladders appeared to have almost a complete lack of erythema and hypervascularity, and only minimal edema was apparent (FIG. 6A). Histologic evaluation revealed mild edema in the submucosa, but no evidence of edema in the lamina propria. Strikingly, no evidence of PMNs were observed throughout all layers of the bladder, along with no evidence of PMNs rolling or marginating out of blood vessels (FIG. 6C). Overall, the GM-1111 pre-treated tissues almost resembled non-inflamed saline control tissues. Inflammatory quantification with tissue MPO assay, comparing LL-37 inflamed bladders vs. group 2 tissues, revealed a 22.3-fold diminished inflammatory response in GM-1111 pre-treated bladders (FIG. 6E) (LL-37 MPO activity 849 ng/ml vs. group 2 pre-treatment with GM-1111 MPO activity 38 ng/ml). Both the histologic findings and MPO results suggested that pre-treatment of bladder tissues with GM-1111 could serve as an important protective therapeutic.

Figure 7:
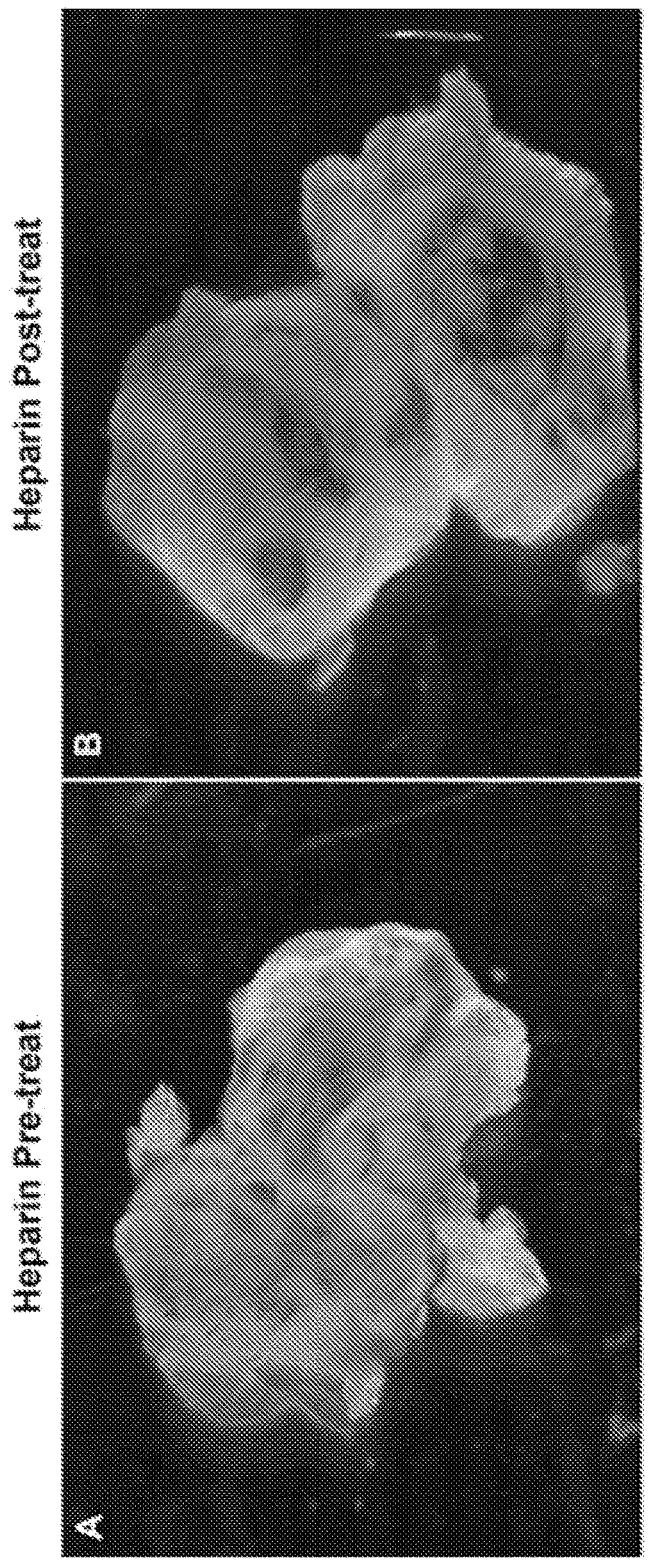
FIG. 7 shows gross images (bladders hemisected exposing inner mucosal surface) of heparin (10 mg/ml) pre-coat/treatment prior to LL-37 instillation (A) versus heparin (10 mg/ml) post-treatment after LL-37 instillation (B). All tissues harvested after 24 h. Significant inflammation observed in (A), edema, hypervascularity, & hemorrhage apparent. Significant inflammation observed in (B), similar levels of edema, hypervascularity, & hemorrhage apparent. Panels (C) & (D) tissue histology ((C) corresponds to (A), (D) corresponds to (B)). Heparin pre-coat/treatment (C) yielded urothelial ulceration (U), edema in the submucosa (SBM) & lamina propria (LP), PMNs present throughout all layers, and PMNs marginating out of blood vessels. Similar inflammatory histology was observed for the heparin post-treated samples (D). Panel (E) represents tissue MPO assay for heparin pre-coat/treatment, illustrating a slight reduction in MPO activity in pre-treated samples (purple bar). Panel (F) represents tissue MPO assay for heparin post-treatment, illustrating no significant reduction in MPO activity in post-treated samples (purple bar). All histology images at 10× magnification.
Figure 7:
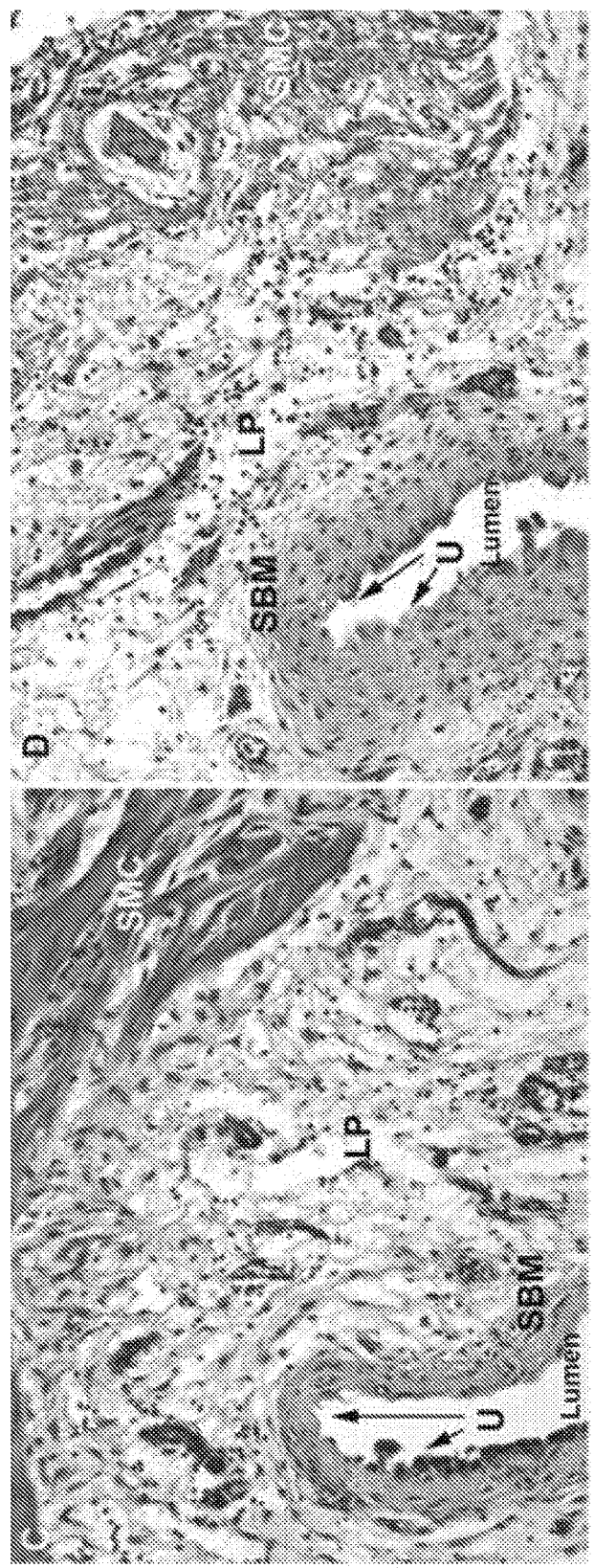
Figure 7:
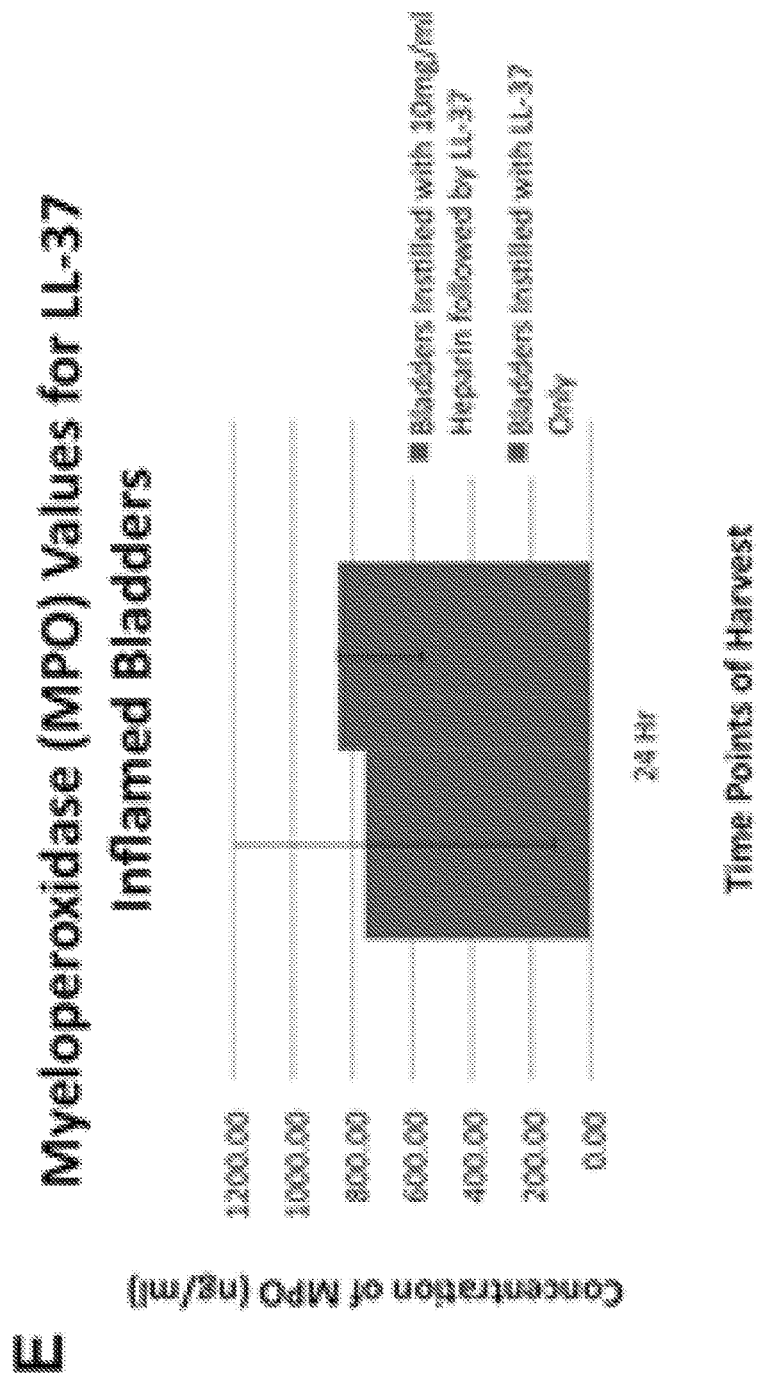
Figure 7:
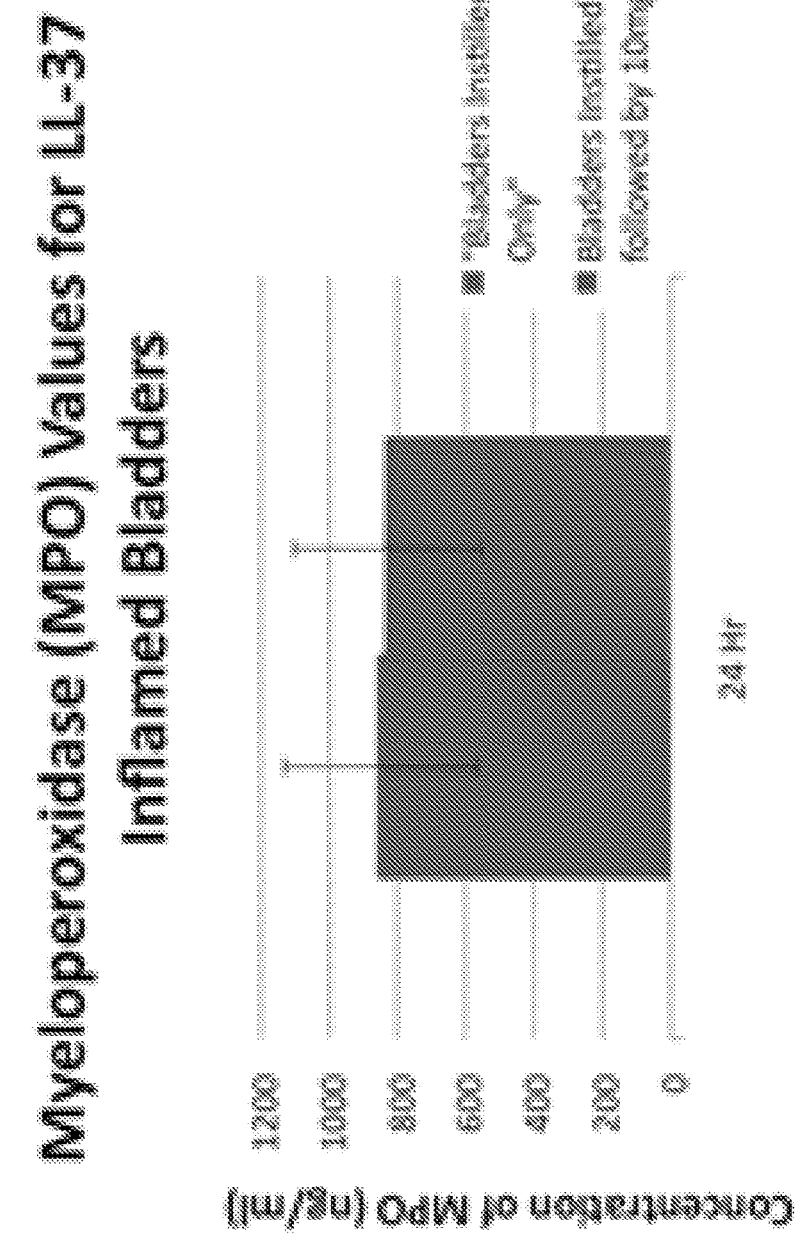

The heparin treated bladders yielded sub-optimal anti-inflammatory results. In group 1 (post-treatment) gross results revealed significant inflammation with edema, hypervascularity and hemorrhage all apparent (FIG. 7B). Histologic findings were consistent, yielding urothelial ulceration, submucosa and lamina propria edema, PMNs abundant throughout all tissue layers, and PMNs marginating from blood vessels (FIG. 7D). MPO assays (FIG. 7F) revealed almost negligible differences in inflammatory activity between untreated LL-37 challenged bladders and heparin post-treated tissues (LL-37 MPO activity 849 ng/ml vs. group 1 post-treatment with heparin MPO activity 827 ng/ml). In group 2 (pre-treatment) gross results revealed similar findings to group 1, with significant inflammation in the form of edema, hypervascularity and hemorrhage all apparent (FIG. 7A). Histologic findings mirrored group 1 as well, with urothelial ulceration, submucosa and lamina propria edema, PMNs present throughout all tissue layers, and PMNs marginating from blood vessels (FIG. 7C). MPO assays (FIG. 7E) revealed only slight differences in inflammatory activity between untreated LL-37 challenged bladders and heparin pre-treated tissues (LL-37 MPO activity 849 ng/ml vs. group 2 pre-treatment with heparin MPO activity 759 ng/ml).

GM-1111 as a "Bladder Armor" Agent

Figure 8:
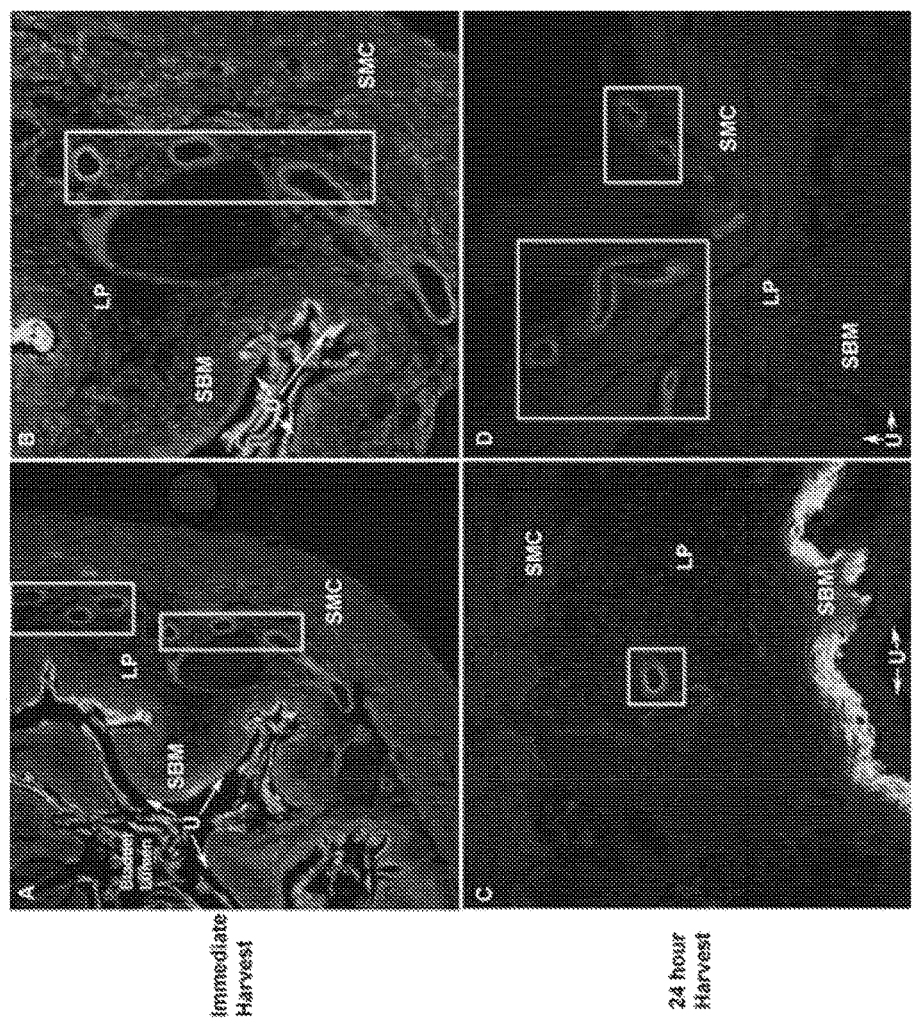
FIG. 8 shows the use of GM-1111 coating as a "bladder armor". Panels (A) & (B) represent immediately harvested tissues after GM-1111 (10 mg/ml) instillation. (A)—low power (10×), (B)—high power (20×). (A) & (B) illustrate uniform GM-1111 coating (green fluorescence) of the urinary GAG layer adjacent to urothelium (U), along with deeper penetration into the submucosa (SBM), lamina propria (LP), and superficial smooth muscle (SMC) layer. Endothelial cells lining arterioles illustrated significant coating by GM-1111 on both basal and luminal sides (rectangles). Panels (C) & (D) represent tissues harvested 24 h after GM-1111 (10 mg/ml) instillation. Both (C) & (D) imaged at 20× magnification. No evidence of GM-1111 along the urinary GAG layer, but was still strongly apparent within select regions of the SBM & along the endothelium lining small arterioles on both basal and luminal sides (rectangles). GM-1111 was still apparent intercalating in random regions of the SMC layer.

In order to better elucidate the tissue coating and penetration properties of the modified hyaluronans, a 10 mg/ml solution of the fluorescently labeled AlexaFluor 633-GM-1111 was instilled and harvested tissues immediately (t=0) after a single 45 min dwell time instillation and also tissues after 24 h (t=24). Processed tissues were also stained with DAPi in order to identify all cellular nuclei. Initial results for the immediate harvest group showed uniform coating of the superficial urinary GAG layer adjacent to the urothelium, along with deeper penetration into the submucosa, lamina propria, and superficial smooth muscle layer (FIGS. 8A & 8B). In addition, endothelial cells lining arterioles illustrating significant coating on both the basal and luminal sides of these vascular structures with GM-1111. No evidence of coating GM-1111 was observed in the endothelium lining venules. Results for the 24 h harvest group yielded no evidence of the presence of GM-1111 along the urinary GAG layer that was previously observed in the immediate harvest group. Importantly, GM-1111 was still strongly apparent within regions of the submucosa and along the endothelium lining small arterioles on both basal and luminal sides (FIGS. 8C & 8D). Finally, GM-1111 was still visualized intercalating in random regions of the bladder smooth muscle. These results indicated that one single exposure of GM-1111 still persisted in the bladder after a 24 h period.

II. Evaluation of Partially and Fully Sulfated Hyaluronan
Preparation of Sulfated Low Molecular Weight Hyaluronan (LMW-HA) from Base-Treated Hyaluronan a. Base-treated LMW HA HA (2 g, 67 kDa) was dissolved in 20 mL of NaOH (40% w/v) in a 100 mL beaker and the mixture was stirred for 2 h at room temperature to partially depolymerize the HA by inducing strand cleavage. The resulting viscous liquid was transferred to a 400 mL beaker that contained 100 mL of isopropanol and stirred for 24 h at room temperature. The resulting solution was gravity filtered (filter paper) and the crude product was collected, dissolved in 250 mL of distilled water, and the pH was adjusted to 7.0. The solution was dialyzed against distilled water for 24 h, changing the water bath 4 times during this period, and then lyophilized to dryness to obtain 1.2 g of the base-treated HA. The size of this product can be determined by HPLC<GPC or electrophoresis, and is generally in the range of 5 kDa to 20 kDa.

b. LMW Partially O-Sulfated Base-treated HA

To obtain the tributylamine (TBA) salt of LMW HA, 0.2 mL of TBA was added to base-treated HA (0.2 g) in 20 mL of distilled water. The mixture was stirred vigorously and lyophilized to dryness. The resulting salt (LMW HA-TBA) was dissolved in 20 mL of N,N-dimethylformamide (DMF) to which the required excess (6 mol/equivalent of total hydroxyl groups in HA, 4 per disaccharide) of pyridine-sulfur trioxide complex (0.325 g) was added. After 3 hours at 40° C., the reaction was quenched by addition of 20 mL of water, and the crude material was precipitated by adding 30 mL of cold ethanol saturated with anhydrous sodium acetate. The crude sulfated product was collected by filtration, dissolved in distilled water (30 mL) and dialyzed against 100 mM NaCl solution (changing solution six times) and against water (change water two times) for two days, changing the solution four times a day, and lyophilized to dryness. The yield of the product was 61% (0.22 g). Based on $^1$H NMR, the degree of substitution was approximately 0.5-1. Elemental analysis gave a sulfur content of 4.13%. The average molecular weight was determined by GPC to be 6,100, and the polydispersity was 2.3.

c. LMW Fully O-Sulfated Base-treated HA

To obtain the tributylamine (TBA) salt of HA, 0.2 mL of TBA was added to base-treated HA (0.2 g) in 20 mL of distilled water. The mixture was stirred vigorously and lyophilized to dryness. The resulting salt (LMW HA-TBA) was dissolved in 20 mL of N,N-dimethylformamide (DMF) to which the required excess (16 mol/equivalent of available hydroxy group in HA) of pyridine-sulfur trioxide complex (11.0 g) was added. After 3 h at 40° C., the reaction was quenched by the addition of 20 mL of water and the crude product was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to dryness to give 0.26 g of product (60% yield). The product was characterized by $^1$H NMR and showed an approximate substitution degree of about 3.5. Elemental analysis gave a sulfur content of 13.22%. The average molecular weight was determined by GPC to be 5,900, with a polydispersity of 2.2.

Preparation of Sulfated Low Molecular Weight Hyaluronan (LMW-HA) from Acid-Treated Hyaluronan a. Fully O-Sulfated Low MW HA (F-OSHA(1)-10,000)

To obtain the tributylamine (TBA) salt of HA, 0.2 mL of TBA was added to HA (0.2 g, ca. 10,000 Da, degraded from 1.3 MDa HA) in 20 mL of distilled water. The mixture was mixed vigorously and lyophilized to dryness. The resulting salt (HA-TBA) was dissolved in 20 mL of N,N-dimethylformamide (DMF) to which the required excess (6 mol/equivalent of available hydroxyl groups in HA) of pyridine-sulfur trioxide complex (0.325 g) was added. After 3 h at 40° C., the reaction was quenched by the addition of 20 mL of water and the crude material was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to dryness to give 0.19 g of product (58% yield). Elemental analysis gave a sulfur content of 12.62%, indicating sulfation of 3.0-3.5. The molecular weight was less than 3,000 Da, suggesting acidic depolymerization during sulfation and workup.

b. Fully O-Sulfated Low MW HA (F-OSHA(2)-10,000)

To obtain the tributylamine (TBA) salt of HA, 0.2 mL of TBA was added to acid-modified 10,000 MW HA (0.2 g) in 20 mL of distilled water. The mixture was mixed vigorously and lyophilized to dryness. The resulting salt (HA-TBA) was dissolved in 20 mL of DMF to which the required excess (16 mol/equivalent of available hydroxyl group in HA) of pyridine-sulfur trioxide complex (1.1 g) was added. After 3 hours at 40° C., the reaction was quenched by addition of 20 mL of water and the crude material was precipitated by adding 30 mL of cold ethanol saturated with anhydrous sodium acetate. The sulfated product was collected by filtration, dissolved in distilled water (30 mL), and dialyzed against 100 mM NaCl solution (changing solution six times) and against water (change water two times) for two days, changing the solution four times a day, and lyophilized to give 0.23 g of product (62% yield). The product was characterized by $^1$H NMR and showed a substitution degree of 3.0-3.5. Elemental analysis gave a sulfur content of 12.10%. The molecular weight was less than 3,000 Da.

c. Fully O-Sulfated Low MW HA (Kewpie Hyalo-Oligo-Pyr.SO$_3$)

Kewpie Hyalo-Oligo HA (200 mg, 0.5 mmole, 8.4 kDa) was dissolved in 10 mL of DMF. TBA (1 eq. 0.5 mmole, 0.12 mL) was added while stirring and stirred for an additional 10 minutes. The required excess (6 mol/equivalent of available hydroxyl groups in HA) of pyridine-sulfur trioxide complex (24 eq. 12 mmole, 1.916 g) was added. After stifling for 3 hours at 40° C., the reaction was quenched by the addition of 15 mL of water, and the crude material was precipitated by adding 25 mL of cold ethanol saturated with anhydrous sodium acetate. The sulfated product was collected by filtration, dissolved in 25 mL of distilled water and dialyzed against 100 mM NaCl solution (changing solution six times) and against water (changing water two times) for two days, changing the solution four times a day, and lyophilized to dryness to give 0.175 g of product (51% yield). The product was characterized by $^1$H NMR and showed a substitution degree of greater than 3.5. The average molecular weight was determined by GPC to be 6,800 Da with a polydispersity of 1.88.

d. Fully O-Sulfated Low MW HA (Novozymes-Pyr.SO$_3$)

Novozymes HA (200 mg, 0.5 mmole) degraded to 11 kDa was dissolved in 10 mL of DMF. TBA (1 eq. 0.5 mmole, 0.12 mL) was added while stifling, and the mixture was stirred for an additional 10 minutes. The required excess (6 mol/equivalent of available hydroxyl groups in HA) of pyridine-sulfur trioxide complex (24 eq. 12 mmole, 1.916 g) was next added. After stifling for 3 hours at 40° C., the reaction was quenched by the addition of 15 mL of water, and the crude material was precipitated by adding 25 mL of cold ethanol saturated with anhydrous sodium acetate. The sulfated product was collected by filtration, dissolved in 25 mL of distilled water and dialyzed against 100 mM NaCl solution (changing solution six times) and against water (changing water two times) for two days, changing the solution four times a day, and lyophilized to dryness to give 0.194 g of product (57% yield). The product was characterized by $^1$H NMR and showed a substitution degree of about 3.0-3.5. The average molecular weight was determined by GPC to be 8,100 Da with a polydispersity of 2.00.

e. Partially O-Sulfated Low MW HA (Novozymes-Pyr.SO$_3$)

Novozymes HA (400 mg, 1.0 mmole) degraded to 11 kDa was dissolved in 25 mL of DMF. TBA (1 eq. 1.0 mmole, 0.24 mL) was added while stifling, and stirred for an additional 10 minutes. The required excess (3 mol/equivalent of available hydroxyl groups in HA) of pyridine-sulfur trioxide complex (12 eq. 12 mmole, 1.908 g) was added. After stifling for 3 hours at 40° C., the reaction was quenched by the addition of 30 mL of water, and the crude material was precipitated by adding 50 mL of cold ethanol saturated with anhydrous sodium acetate, and then collected by filtration. The resulting crude partially O-sulfated HA was dissolved in 40 mL of distilled water and dialyzed against 100 mM of NaCl solution (changing solution six times) and against water (changing water two times) for two days, changing the solution four times a day, and lyophilized to dryness to give 0.386 g of product (56% yield). The product was characterized by $^1$H NMR and showed a substitution degree of 2.0. The average molecular weight was determined by GPC to be 9,500 Da with a polydispersity of 1.77.

f. Fully O-Sulfated Low MW HA (Novozymes-DMF.SO$_3$)

Novozymes HA (200 mg, 0.5 mmole) degraded to 11 kDa was dissolved in 10 mL of DMF. TBA (1 eq. 0.5 mmole, 0.12 mL) was added while stifling, and the mixture was stirred for an additional 10 minutes. The required excess (6 mol/equivalent of available hydroxyl groups in HA) of DMF-sulfur trioxide complex (24 eq. 12 mmole, 1.836 g) was added. After stirring for 3 hours at 30° C., the reaction was quenched by the addition of 15 mL of water, and the crude material was precipitated by adding 25 mL of cold ethanol saturated with anhydrous sodium acetate, and then collected by filtration. The resulting crude fully O-sulfated HA was dissolved in 25 mL of distilled water and dialyzed against 100 mM of NaCl solution (changing solution six times) and against water (changing water two times) for two days, changing the solution four times a day, and lyophilized to dryness to give 0.057 g of product (17% yield). The product was characterized by $^1$H NMR and showed a substitution degree of about 3.0-3.5. The average molecular weight was determined by GPC to be 1,900 Da with a polydispersity of 2.48.

FIG. 3a shows native polyacrylamide gel electrophoresis (PAGE) analysis of (A) FOS HA (2) 10 kDa, (B) FOS HA (1) 10 kDa, (C) FOS BHA, and (D) POS BHA. 10 µg of each sample was separated on a Novex® Tris-Glycine 18% gel (Invitrogen, Carlsbad, Calif.) run at 125 V for 1.5 hours under native conditions. FIG. 3b shows native PAGE analysis of (E) FOS HA manufactured from Kewpie's Hyalo Oligo HA using pyridine-sulfur trioxide complex, (F) FOS HA manufactured from Novozymes HA using pyridine-sulfur trioxide complex, (G) POS HA manufactured from Novozymes HA using pyridine-sulfur trioxide complex, and (H) FOS HA 10 kDa manufactured from sulfur trioxide N,N-dimethylformamide complex. 15 µg of each sample was separated on a 20% acrylamide IDSmart Gel (Boca Scientific, Boca Raton, Fla.) run at 125 V for 75 minutes under native conditions. Gels were stained in an aqueous solution of 0.08% azure A.

g. Fully O-Sulfated Low MW HA (GM-0111)

HA (5.0 g of 5.4 kDa degraded from 950 kDa HA, Novozymes) was suspended in 400 mL N,N-dimethylformamide (DMF) and 3.0 mL (1 eq.) of tributylamine (TBA) was added. The solution was stirred for 5 minutes. Pyridine-sulfur trioxide complex (24 eq., 48.4 g) was added in six portions and the mixture was stirred for 3 hours at 40° C. The reaction was quenched by the addition of 100 mL of water and the crude material was precipitated by adding 500 mL of cold ethanol saturated with anhydrous sodium acetate. The sulfated product was collected by filtration, dissolved in distilled water (650 mL) and dialyzed against 100 mM NaCl solution (changing solution six times) and against water (changing water two times) for two days, changing the solution four times a day, and lyophilized to dryness to give 4.6 g of product (51% yield). Elemental analysis gave a sulfur content of 13.5%, indicating sulfation of 3.0-3.5 SD. The molecular weight was determined by gel permeation chromatography to be 5.1 kDa with a polydispersity of 1.9.

Anti-Coagulant Properties and Toxicity

GM-0111 was extremely well tolerated and did not produce any signs of toxicity when administered orally to C57BL/6J mice at a single bolus dose of 2,000 mg/kg. In addition, necropsy findings did not indicate any abnormalities 24 hours after the oral administration of GM-0111.

In Vitro Studies a. Human Leukocyte Elastase (HLE) Inhibition Assay

To investigate the inhibitory effects of sulfated HA on leukocyte elastase, 100 µl of 7.5 µg/ml HLE was incubated with 100 µl of sulfated HA's at a range of concentrations from 0.001 to 100 µg/mL. The mixture was incubated for 10 minutes at 25° C., after which 50 µl of the HLE substrate suc-Ala-Ala-Val-pNA (1.5 mM) was added. Active HLE cleaves the substrate and produces chromogenic pNA which is followed by measuring the change in absorbance at 405 nm using a kinetic read. $IC_{50}$ values are obtained (Table 1) using a 4-parameter logistic non-linear regression equation of the Vmax (rate of absorption) versus sulfated HA concentration.

TABLE 1

Inhibition of Human Leukocyte Elastase (HLE)

| Sample | $IC_{50}$ value (µg/ml) |
|---|---|
| POS BHA | 0.30 |
| FOS BHA | 0.18 |
| F-OSHA(2) 10k | 0.23 |
| F-OSHA(1) 10k | 0.22 |
| FOSHA Kewpie | 0.46 |
| FOSHA Novozymes | 0.45 |
| POSHA Novozymes | 0.47 |
| FOSHA Novozymes DMF | 0.76 |

In vitro studies showed that GM-0111 inhibited human leukocyte elastase with an $IC_{50}$ of 430 ng/mL. GM-0111-03 inhibited RAGE binding to its ligands with $IC_{50}$'s of 36 ng/mL for CML-BSA, 60 ng/mL for S-100 protein, and 91 ng/mL for HMGB1.

b. CML-BSA/RAGE Complex Inhibition Assay

The CML-BSA and RAGE complex inhibition assay was prepared by coating a polyvinyl chloride plate with 100 µl of 5 µg/ml CML-BSA. Separately, a 1 µg/ml solution of RAGE-Fc chimera in PBST-0.1% BSA was incubated with an equal volume of serially diluted sulfated low molecular weight hyaluronan and HA oligosaccharides at concentration ranges of 0.0005 µg/ml to 100 µg/ml overnight at 4° C. The following day, 50 µl of RAGE-sulfated HA mix was transferred to each respective ligand-coated well and incubated at 37° C. for 1 hour. Wells were then washed four times with PBST. To detect bound RAGE, 50 µl of 0.5 µg/ml of anti-RAGE antibody was added to each well. The plate was incubated for 1 hour at room temperature and the wells washed again four times with PBST. HRP-conjugated secondary antibody (50 µl per well) was added, wells were incubated for 1 hour at room temperature and then washed four times with PBST. A colorimetric reaction was initiated by addition of 100 µl of TMB and terminated with the addition of 50 µl of 1 N HCl. Absorbance at 450 nm was plotted against the sulfated HA concentration and $IC_{50}$ values obtained (Table 2) using a 4-parameter logistic non-linear regression equation.

TABLE 2

Inhibition of CML-BSA binding to RAGE

| Sample | $IC_{50}$ value (µg/ml) |
|---|---|
| POS BHA | >100 |
| FOS BHA | 0.0468 |
| F-OSHA(2) 10k | 0.0176 |
| F-OSHA(1) 10k | 0.0197 |
| FOSHA Kewpie | 0.037 |
| FOSHA Novozymes | 0.023 |
| POSHA Novozymes | 0.066 |
| FOSHA Novozymes DMF | 0.521 | c. Characterization of the Pyridinium Adduct

Figure 5:
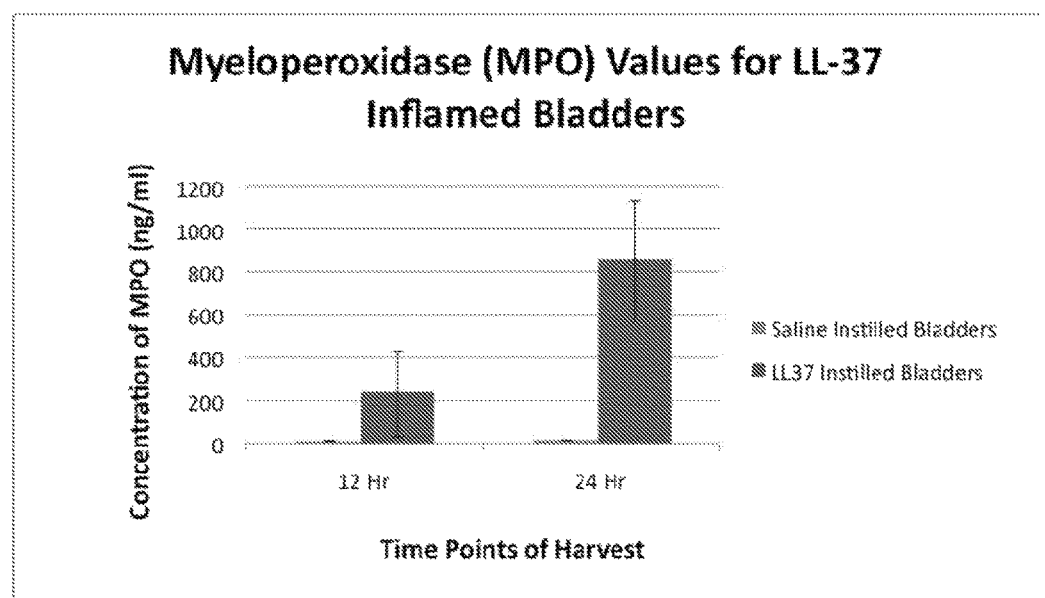
FIG. 5 shows tissue MPO inflammation quantification assay comparing saline control versus LL-37 instilled bladders. Minimal MPO activity in saline control tissues (11 ng/ml after 12 h, 14 ng/ml after 24 h; blue bars). Significant elevation of MPO activity in LL-37 instilled bladders, with continued escalation from 12 h (229 ng/ml) to 24 h (849 ng/ml) (red bars).

The pyridinium content of the sulfated HA samples prepared using the pyridine-sulfur trioxide complex was analyzed via UV absorbance. A standard curve was created using 1-butylpyridinium bromide (Sigma, St. Louis, Mo.) and the sulfated HA samples were diluted from 2 to 0.025 mg/ml as necessary for the UV measurements to fall within the standard curve. Absorbance values at 255 nm in a quartz cuvette were recorded for the standards and samples. From the standard curve, weight percent pyridinium values were calculated for each sample and are included in Table 3. The pyridinium adduct of FOSHA-Kewpie-Pyr.SO$_3$ was also characterized by $^{13}$C NMR spectroscopy and compared to published data. (Hintze V, Moeller S, Schnabelrauch M, Beirbaum S, Viola M, Worch H, Scharnweber D. "Modifications of Hyaluronan Influence the Interaction with Human Bone Morphogenetic Protein-4 (hBMP-4)" Biomacromolecules 10:3290-3297, 2009) The $^{13}$C NMR data is presented in Table 4. Finally, FIG. 5 is the $^1$H NMR spectrum of FOSHA-Kewpie-Pyr.SO$_3$, which reveals three peaks between 8.00 ppm and 9.10 ppm representing the pyridinium protons of the pyridinium adduct.

TABLE 3

Measurement of Pyridinium Content of Sulfated HA Created with Pyridine-Sulfur Trioxide Complex

| Sample | Average wt % pyridinium | Standard deviation |
| --- | --- | --- |
| FOSHA Kewpie | 0.80 | 0.02 |
| FOSHA Novozymes | 0.462 | 0.009 |
| POSHA Novozymes | 0.662 | 0.006 |
| POS BHA | 0.11 | 0.03 |
| FOS BHA | 1.7 | 0.1 |
| F-OSHA(2) 10k | 14.7 | 0.8 |
| F-OSHA(1) 10k | 9.0 | 0.6 |

TABLE 4

$^{13}$C NMR Data of FOSHA-Kewpie-Pyr•SO$_3$ compared with published data.

| | Hya | sHya 1.0 (6.6% S) | sHya2.8 (13.1% S) | FOSHA-Kewpie |
| --- | --- | --- | --- | --- |
| C=O | 175.4 | 175.2 | 175.3 | 174.9 |
| C'=O (6') | 174.4 | 174.2 | 175.0 | 173.9 |
| C1' | 103.6 | 103.5 | 102.0 | 101.4 |
| C1 | 101.0 | 101.3 | 100.6 | 100.4 |
| C3 | 83.5 | 82.5 | 79.3-76.9 | 79.1-75.6 |
| C4' | 80.7 | 81.4 | | |
| C5' | 77.1 | 76.8 | | |
| C5 | 76.2 | 74.2 | | |
| C3' | 74.4 | 73.8 | | |
| C2' | 73.3 | 72.9 | 73.7 | 73.0 |
| C4 | 69.4 | 68.8 | 69.5 (small) | 68.6 |
| C6 | 61.5 | 67.5 | 68.3 | 67.7 |
| C2 | 54.9 | 54.7 | 56.0 | 55.2 |
| CH$_3$ | 23.2 | 22.9 | 23.6 | 23.2 |
| Py 2,6 | | | | 142.7 |
| Py 4 | | | | 128.2 |
| Py 3,5 | | | | 103.4 |

In Vivo Studies a. Mouse Bladder Inflammation Model

Mouse bladders are sensitive to various inflammatory substances including LL-37 (cathelicidin peptide) and have served as an excellent animal model to study the potential therapeutic agents in inflammatory diseases including cystitis. In order to investigate the anti-inflammatory effects of sulfated HA, the protective effects of FOSHA derivatives were measured in a murine cystitis model. First, C57/BL6 adult female mice were anesthetized and a catheter was inserted into the bladder through the urethra. The bladders were washed by infusing and draining 0.9% sterile saline. Bladders were then pre-instilled with either 150 µL of saline, 10 mg/ml FOSHA (Kewpie) or 10 mg/ml FOSHA (Novozymes) for 1 hour. The bladders were emptied and then instilled with 150 µL of 320 µM LL-37 for an additional 1 hour. All animals were fully recovered without complications. Twenty-four hours after the completion of the procedure, the bladders were removed, photographed, and frozen for MPO analysis.

b. Myeloperoxidase (MPO) Assay

The major cellular responses to inflammatory substances are secretion of various cytokines from damaged cells that recruit various immune cells to the target site. MPO is a peroxidase enzyme expressed abundantly in polymorphonuclear cells, which are primary cells recruited to the site of inflammation during the early stage of inflammation and therefore, MPO is an excellent marker to quantitatively measure the degree of inflammation. To analyze the anti-inflammatory effects of fully-sulfated HA in the murine cystitis model, the quantity of expressed MPO was measured in the bladders pre-treated with sulfated HA and compared with the levels of expressed MPO in untreated bladders and a saline control. Bladders were weighed and homogenized. The homogenized samples were centrifuged at 5,000 rpm to separate the soluble fraction from tissue debris and the concentration of MPO in the tissue homogenates (ng/mg tissue) was measured using the mouse MPO ELISA kit (HK210, Hycult biotech, The Netherlands) and expressed as percent difference from the saline instilled control (normal bladder without inflammation). Results are provided in FIG. 2.

To determine whether pretreatments of sulfated HA reduce tissue MPO concentration induced by instilled LL-37, we performed statistical analysis using one-way ANOVA followed by Tukey-Kramer multiple comparisons test using GraphPad InStat software (Version 3.1, GraphPad Software, Inc.). Statistical significance was set at p<0.0.

c. Conclusions

The results from the in vitro studies demonstrate the importance of the degree of sulfation with respect to RAGE antagonist activities (Table 2). Partial sulfation (less than 6% sulfur) results in a much less potent RAGE antagonist. Sulfated HA compounds with a MW less than 2,000 Da also show reduced potency in the in vitro assays. Fully-sulfated HA compounds, including those possessing the pyridinium adduct in excess of 1% w/w, showed good in vivo efficacy in reducing inflammation in the mouse model of bladder inflammation.

Preinstillation Experiments with GM-0111

Additional experiments were conducted to investigate the therapeutic effects of GM-0111, in the murine cystitis model induced with LL-37. Each animal was anesthetized with isoflurane and a flexible catheter inserted into the urinary bladder through the urethral opening (SILASTIC laboratory tubing, 0.30 mm i.d.×0.64 mm o.d., DOW Corning, MI). The urine was drained by gently pressing the abdomen. The bladder was washed by instilling and draining with 150 µL of endotoxin free sterile phosphate buffered saline (PBS, Amresco, Ohio). The emptied bladders were then filled with either 150 µL of PBS or various concentrations of GM-0111 (1, 5, 10, 30, and 100 mg/mL) dissolved in PBS. To increase the contact of GM-0111 with the bladder, the bladder was drained and re-instilled with either PBS or GM-0111. After 1 hr of instillation with GM-0111, the bladder was drained and instilled with the same volume of LL-37 (250 µM) to induce cystitis. The LL-37 instillation procedure was also repeated as per the GM-0111 instillation. One hour after the initial LL-37 instillation, the catheters were removed and the animals were allowed to recover. To minimize damage to the bladder and to reduce vesicoureteral reflux, the solutions were instilled at a flow rate of 2 µL/sec (or 10 µL/5 sec). In addition, possible microorganismal contamination was minimized by sterile filtration of all dissolved materials.

Necropsy and Necropsy Score

Twenty-four hours after LL-37 instillation, animals were deeply anesthetized with isoflurane and the necropsy performed. Whole blood was collected through the caudal vena cava, the animals exsanguinated, and the urinary bladder harvested. The blood was transferred to Microvette tubes (Sarstedt, Germany) to collect serum. The harvested bladders were weighed and halved transversally. The halved bladders were then either stored at −20° C. (as were the serum samples) for biochemical analysis, or stored in 4% formalin for histological evaluation.

During necropsy, the severity of inflammation of the bladder was determined by scoring the presence of hyperemia (0: none and 1: hyperemic) and the degree of edema (0: none, 1: mild, 2: moderate, and 3: marked). The sum of the scores of hyperemia and edema were used as a necropsy score for statistical analysis.

Biochemical Analysis

To determine the generalized reaction in the body by induced cystitis and to investigate the protective effects of GM-0111, the concentration of serum amyloid P (SAP) was measured using an ELISA kit (ICL Laboratories, OR). In order to determine the severity of inflammation in the local tissue, bladders were homogenized in lysis buffer (200 mM NaCl, 10 mM Tris, 10% glycerin) supplemented with protease inhibitor (Halt Protease Inhibitor Cocktail, Thermo Scientific, IL). The tissue activity of myeloperoxidase was measured using the Fluoro MPO™ kit (Cell Technology, CA), and the tissue concentrations of IL-6 and PTX-3 measured by ELISA (BioLegend, CA and R&D Systems, MN).

Histological Evaluation

The formalin fixed tissues were paraffin embedded, sectioned at 4 µm thickness, and stained with hematoxylin and eosin (Histology Services by Charles River Laboratories, MA). The severity of inflammation of each sample was evaluated and quantified by assessing the presence and the extent of edema, polymorphonuclear neutrophilic (PMN) infiltration, and the erosion of urothelial epithelium within each slide according to the following criteria (Table 5).

TABLE 5

Quantification of histological evaluation (histology score).

| Parameter | Degree | Score |
|---|---|---|
| Edema | No edema evident | 0 |
| | Edema limited to submucosal region. The width of submucosal region equal or less than combined width of urothelium and detrusor muscle layer. | 1 |
| | Edema limited to mucosal region. The width of submucosal region greater than combined width of urothelium and detrusor muscle but less than 2 times this width. | 2 |

TABLE 5-continued

Quantification of histological evaluation (histology score).

| Parameter | Degree | Score |
|---|---|---|
| | Edema near detrusor muscle. The width of submucosal region 2-4 times width of urothelium and detrusor muscle. | 3 |
| | Edema in all layers. The width of submucosal region is greater than 4 times width of urothelium and detrusor muscle. | 4 |
| PMN infiltration | None to negligible | 0 |
| | Scant | 1 |
| | Moderate | 2 |
| | Extensive | 3 |
| Urothelial erosion | None | 0 |
| | Thinner | 1 |
| | Presence of denuded area | 2 |
| Histology Score | | Sum (0-9) |

Statistical Analysis

All data from various measurements were individually identified. In order to compare whether preinstillation of GM-0111 produced significantly different changes in observed data compared to PBS treatment, analysis of variance test was performed followed by Dunnett's t-test. Necropsy and histological scores were evaluated with Kruskal-Wallis rank sum test followed by kwmc (multiple comparison) test using pgirmess library using R 2.14.0. The tests were also repeated with data by comparing with the data from the untreated normal animals to determine whether preinstillation of GM-0111 protects the urinary bladder from developing inflammatory changes.

Results

Preinstillation of GM-0111 Prevents the Urinary Bladder from Developing Cystitis In order to determine the protective effects of GM-0111 on the LL-37 induced cystitis model, the bladder was coated with various concentrations of GM-0111 by instilling into the urinary bladder for 1 hr followed by instillation of LL-37 for 1 hr. Twenty-four hours after LL-37 instillation, the animals were sacrificed, necropsy was performed, and the urinary bladder was harvested for biochemical and histological evaluations.

Figure 9:
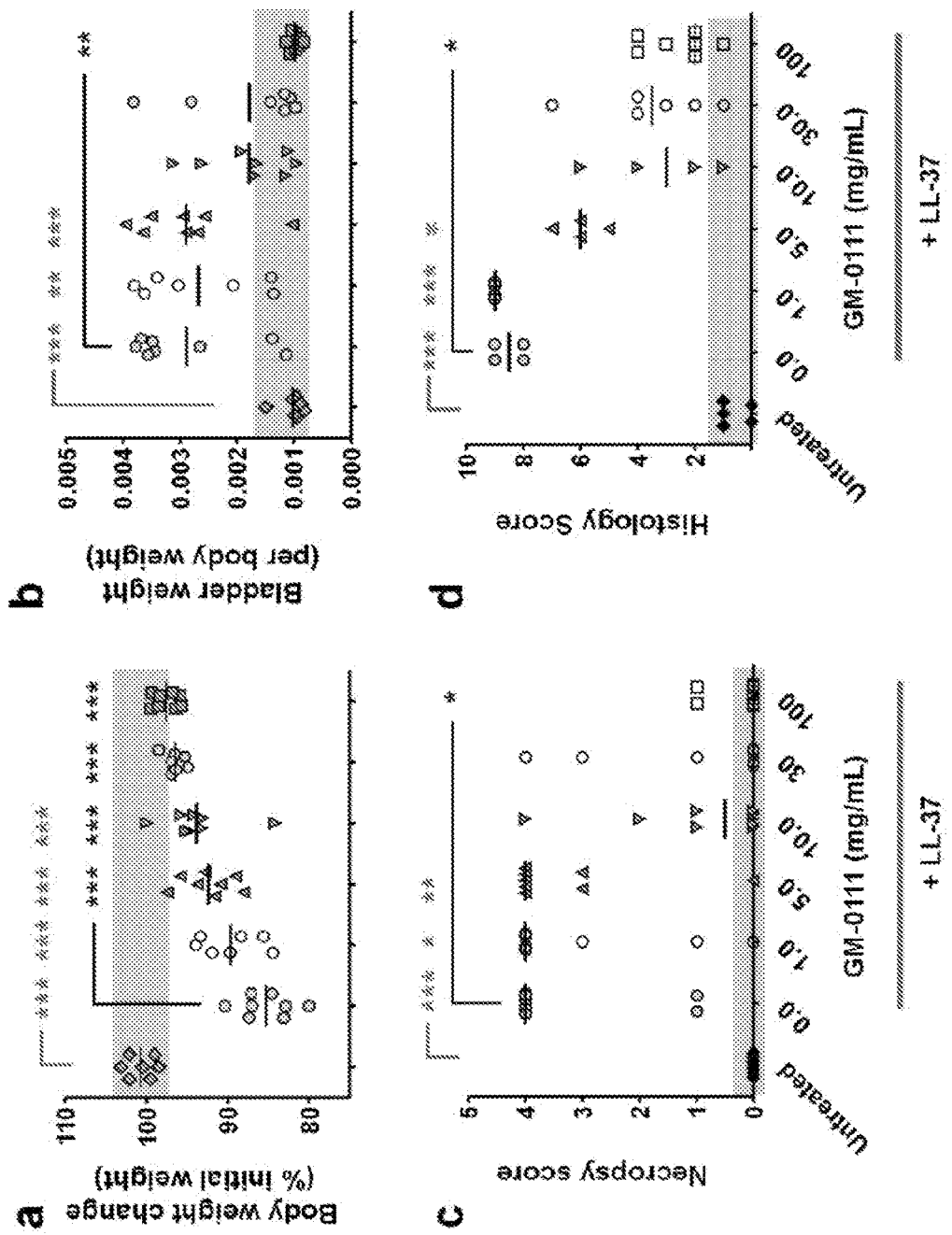
FIG. 9 shows that preinstillation of GM-0111 prevents LL-37 (250 µM) induced cystitis. Data indicate changes of body weights (a), bladder weights per body weights (b), necropsy scores (c), and histology scores (d) 24 hr after intravesical instillation of LL-37. Horizontal lines in each graph indicate mean (a and b) and median values (c and d). Gray colored area indicates the normal range. *$p<0.05$, $p<0.01$, and *$p<0.001$.

During necropsy, the severity of inflammation was determined in each animal by observing gross anatomical changes and by measuring the weight of the bladder. It was discovered that preinstillation of GM-0111 into the urinary bladder reduces the signs of developing cystitis induced by LL-37. The body weight gains in the GM-0111 preinstilled animals were significantly higher than the animals treated with PBS (FIG. 9a). The weight of the edematous urinary bladder increased as a consequence of increased fluid and colloidal proteins in the inflamed tissue. It was discovered that preinstillation of GM-0111 also significantly decreased the weight of the urinary bladder (FIG. 9b) suggesting a reduction in the inflammatory changes induced with LL-37.

Figure 10:
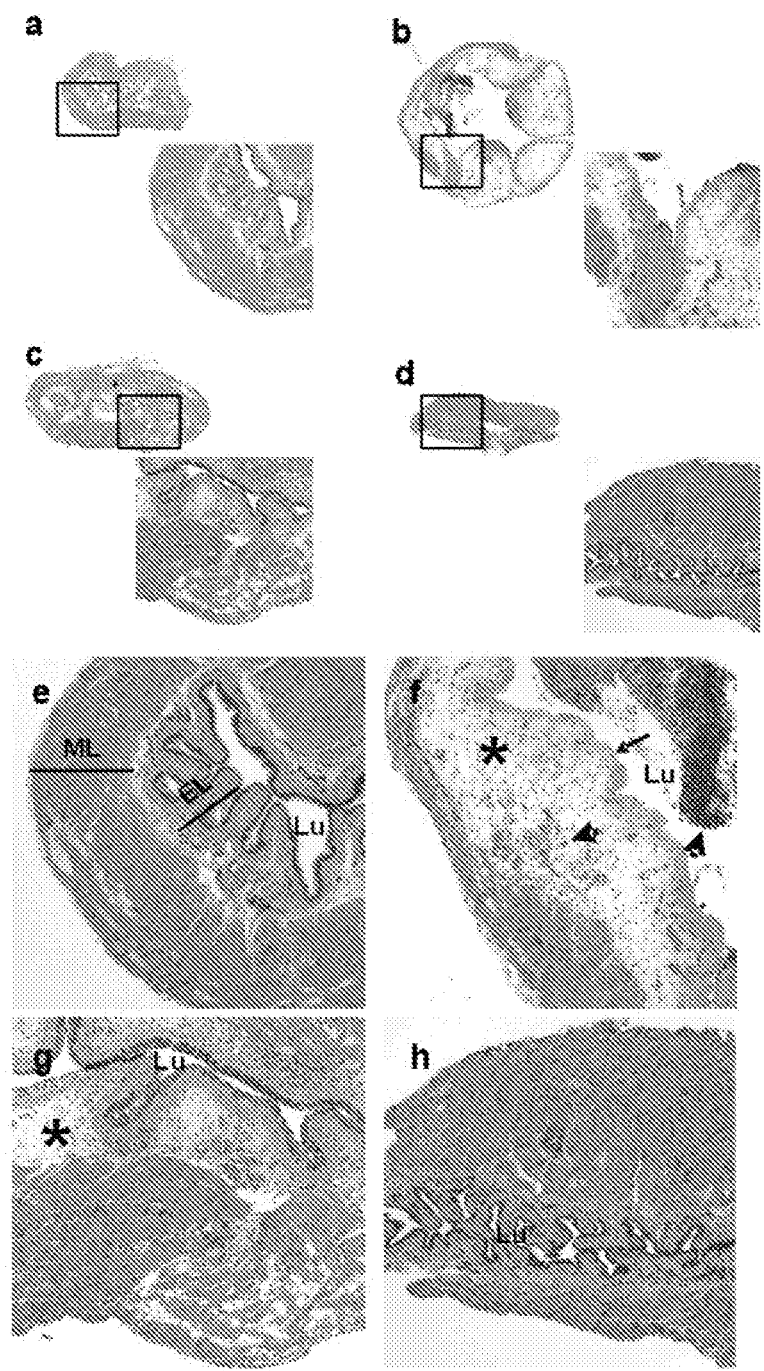
FIG. 10 shows photomicrographs of tissues stained with hematoxylin and eosin show marked inflammatory changes in the urinary bladder 24 hours after instillation of LL-37 (250 µM). Pre-instillation of GM-0111 reduces the severity of inflammatory changes in the urinary bladder in a dose dependent manner as indicated by reduced inflammatory hallmarks—polymorphonuclear neutrophilic infiltration (basophilic areas filled with PMNs, arrow heads), massive edema (*); and denuded epithelial layer (arrow). The urinary bladders from untreated normal (a and e), treated with PBS/LL-37 (b and f), GM-0111 (10 mg/mL)/LL-37 (c and g), and GM-0111 (100 mg/mL)/LL-37 (d and h). ML: muscular layer, EL: epithelial layer, and Lu: lumen. Panoramic view of images (a-d) and closer view of boxed areas (e-h) with original magnification at 5×.

Instilling LL-37 (250 µM) into the urinary bladder induced inflammatory changes with hallmarks that include the infiltration of polymorphonuclear neutrophils (PMNs) into submucosal layer, increased vascularization, hemorrhage, extensive edema throughout all layers of the urinary bladder, and thinning and erosion of the urothelial layer (FIG. 10e vs. 10f). The presence of increased fluid and vascularization leads to the typical appearance of the urinary bladder, hyperemic and large (FIG. 10a vs. 10b). To evaluate gross observations more closely, the histological changes of the urinary bladder preinstilled with GM-0111 were investigated. Preinstillation of GM-0111 significantly reduced the severity of the inflammatory signs which are easily observable from a dose as low as 5 mg/mL as indicated by the reduced extent of edema and the fewer number of PMNs along with an intact urothelial layer in the GM-0111 preinstilled urinary bladders compared to the PBS preinstilled urinary bladders (FIG. 10b vs. 10c and 10d). The histological appearances of the urinary bladders preinstilled with GM-0111 from 10 mg/mL and higher concentrations were close or similar to the untreated normal bladders (FIG. 10e vs. 10g and 10h).

Figure 11:
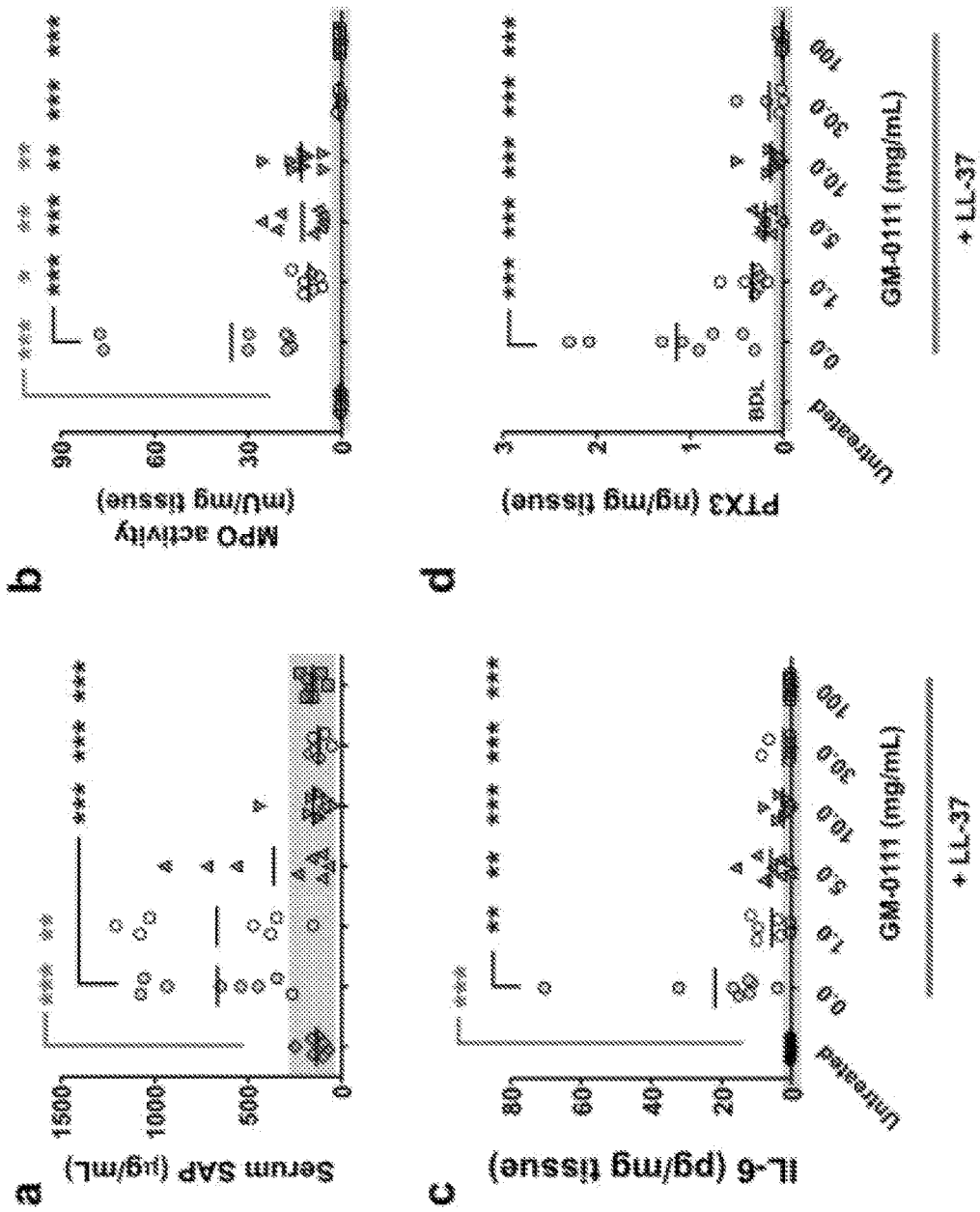
FIG. 11 shows preinstillation of GM-0111 prevents LL-37 (250 µM) induced cystitis. Data indicate serum concentrations of SAP (a), tissue activity of MPO (b), tissue concentrations of IL-6 (c), and PTX3 (d) 24 hr after intravesical instillation of LL-37. Horizontal lines in each graph indicate mean values. Gray colored area indicates the normal range. $p<0.01$, and *$p<0.001$.

In order to investigate the mechanism of GM-0111 in reducing LL-37 mediated inflammatory changes in the bladder and in improving the general health of the animals, the changes of various biochemical markers in the urinary bladder and in the serum were investigated. First, the tissue activities of myeloperoxidase (MPO) was determined. The primary source of MPO is the neutrophilic granular leukocytes mainly used to clear pathogens during inflammation. The mean tissue activities of MPO in the urinary bladders preinstilled with PBS were 114-fold higher than that in the tissues from untreated normal animals (FIG. 11b). Preinstillation of GM-0111 significantly lowered the tissue activities of MPO even at 1 mg/mL (FIG. 11b). Next, we determined the tissue concentrations of IL-6, which is one of the major proinflammatory cytokines released by various cells upon inflammatory stimuli. It was discovered that the concentrations of IL-6 in the urinary bladders preinstilled with PBS were approximately 70-fold higher than that in the normal urinary bladders (FIG. 11c). Preinstillation of GM-0111 sharply reduced the concentrations of IL-6 in the tissue similar to the level in the normal urinary bladders even at the 1.0 mg/mL concentration of GM-0111. We also have sought an independent tissue marker that changes upon inflammatory stimuli with LL-37. PTX3 is a novel member of long pentraxin family that increases in the tissue or in the serum upon various inflammatory stimuli. Consistent with the data from MPO and IL-6 measurements, the tissue concentrations of PTX3 markedly increased from undetectable levels to 1.1 ng/mg tissue preinstilled with PBS (FIG. 11d). These increases were significantly reduced by preinstillation of GM-0111 even at 1 mg/mL and many remained below detection level (lower than 2 µg/mL of tissue) in the tissue preinstilled with 10 mg/mL and higher concentrations of GM-0111. These data suggest that the protective effects of GM-0111 against LL-37 induced cystitis are significant and can be obtained by preinstilling GM-0111 as low as 1 mg/mL concentration.

A possible biomarker present in the blood was investigated in order to monitor the progression of cystitis in the model. Serum amyloid P (SAP) is a short pentraxin similar to C-reactive protein (CRP) produced and secreted by the liver in mammals. SAP has been known to sharply increase in response to rising levels of pro-inflammatory cytokine IL-6 in rodents. It was tested whether the increased tissue concentrations of IL-6 by LL-37 also raised the serum concentrations of SAP as well as determine whether preinstillation of GM-0111 affects the concentrations of SAP. The measurements indicate that the concentrations of SAP in PBS preinstilled animals are approximately 5-fold higher than that in the untreated normal animals (FIG. 11a). However, SAP levels in GM-0111 (10 mg/mL or higher) preinstilled animals were significantly lower than that in the PBS preinstilled animals. These data are consistent with the histological evaluations suggesting that SAP may be a good biomarker indicating the inflammatory changes in the tissues.

Overall, the data from various biochemical and histological analyses suggest that GM-0111 is a very powerful compound at preventing and reducing the severity of inflammation in the bladder induced with LL-37. The protective effects of GM-0111 can be observed as low as 1 mg/mL and the strong protective effects appear from 10 mg/mL with safe use up to 100 mg/mL in our animal model.

Throughout this application, various publications are referenced. The disclosures of these publications in their entireties are hereby incorporated by reference into this application in order to more fully describe the compounds, compositions and methods described herein. Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES

1. Theoharides, T.; Sant, G., New agents for the medical treatment of interstitial cystitis. *Expert Opin. Investig. Drugs* 2001, 10, 521-546.
2. Theoharides, T., Treatment approaches for painful bladder syndrome/interstitial cystitis. *Drugs* 2007, 67, 215-235.
3. Toft, B.; Nordling, J., Recent developments of intravesical therapy of painful bladder syndrome/interstitial cystitis: a review. *Curr. Opin. Urol.* 2006, 16, 268-272.
4. Lukban, J.; Whitmore, K.; Sant, G., Current management of interstitial cystitis. *Urol. Clin. N. Am.* 2002, 29, 649-660.
5. Theoharides, T.; Cochrane, D., Critical role of mast cells in inflammatory diseases and the effect of acute stress. *J. Neuroimmunol.* 2004, 146, 1-12.
6. Jones, C. A.; Nyberg, L., Epidemiology of interstitial cystitis. *Urology* 1997, 49, (5A Suppl), 2-9.
7. Payne, C. K.; Joyce, G. F.; Wise, M.; Clemens, J. Q., Interstitial cystitis and painful bladder syndrome. *J Urol* 2007, 177, (6), 2042-9.
8. Parsons, C.; Housley, T.; Schmidt, J.; Lebow, D., Treatment of interstitial cystitis with intravesical heparin. *Br. J. Urol.* 1994, 73, 504-507.
9. Baykal, K.; Senkul, T.; Sen, B.; Karademir, K.; Adeyener, C.; Erden, D., Intravesical heparin and peripheral neuromodulation on interstitial cystitis. *Urol. Int.* 2005, 74, 361-364.
10. Parsons, C., Successful downregulation of bladder sensory nerves with combination of heparin and alkalinized lidocaine in patients with interstitial cystitis. *Urology* 2005, 65, 45-48.
11. Anderson, V.; Perry, C., Pentosan polysulfate: a review of its use in the relief of bladder pain or discomfort in interstitial cystitis. *Drugs* 2006, 66, 821-835.
12. Sant, G.; Propert, K.; Hanno, P.; Burks, D.; Culkin, D.; Diokno, A.; Hardy, C.; Landis, J.; Mayer, R.; Madigan, R.; Messing, E.; Peters, K.; Theoharides, T.; Warren, J.; Wein, A.; Steers, W.; Kusek, J.; Nyberg, L., A pilot clinical trial of oral pentsan polysulfate and oral hydroxyzine in patients with interstitial cystitis. *J. Urol.* 2003, 170, 810-815.
13. Iavazzo, C.; Athanasiou, S.; Pitsouni, E.; Falagas, M., Hyaluronic acid: an effective alternative treatment of interstitial cystitis, recurrent urinary tract infections, and hemorrhagic cystitis? *Europ. Urol.* 2007, 51, 1534-1541.

14. Theoharides, T.; Sant, G., A pilot open label of Cysto-Protek in interstitial cystitis. *Int. J. Immunopathol. Pharmacol.* 2005, 18, 183-188.
15. Steinhoff, G.; Ittah, B.; Rowan, S., The efficacy of chondroitin sulfate 0.2% in treating interstitial cystitis. *Can. J. Urol.* 2002, 9, 1454-1458.

What is claimed is:

1. A method for treating or preventing urological inflammation in a subject comprising administering to the subject an effective amount of a sulfated hyaluronan or the pharmaceutically acceptable salt or ester thereof, wherein (1) 100% of the primary C-6 hydroxyl protons of the N-acetylglucosamine residue of the sulfated hyaluronan are substituted with a sulfate group, (2) the sulfated hyaluronan has a degree of sulfation from 3.0 to 4.0, and (3) the sulfated hyaluronan has an average molecular weight from 1 kDa to 3 kDa.

2. The method of claim 1, wherein at least one C-2 hydroxyl proton and C-3 hydroxyl proton of a uronic acid residue and at least one C-4 hydroxyl proton of an N-acetylglucosamine residue of hyaluronan is substituted with a sulfate group.

3. The method of claim 1, wherein the pharmaceutically acceptable ester is a prodrug.

4. The method of claim 1, wherein the compound is administered as a pharmaceutical composition.

5. The method of claim 4, wherein the composition is administered transmucosally.

6. The method of claim 4, wherein the composition is administered transmucosally, wherein the transmucosal administration comprises vaginal or by intravesical instillation.

7. The method of claim 4, wherein the composition further comprises an anti-inflammatory agent, an anti-pyretic agent, steroidal and non-steroidal drugs for anti-inflammatory use, a hormone, a growth factor, a contraceptive agent, an antiviral, an antibacterial, an antifungal, an analgesic, a hypnotic, a sedative, a tranquilizer, an anti-convulsant, a muscle relaxant, a local anesthetic, an antispasmodic, an antiulcer drug, a peptidic agonist, a sympathiomimetic agent, a cardiovascular agent, an antitumor agent, or an oligonucleotide.

8. The method of claim 1, wherein the pharmaceutically acceptable salt of the compound is an organic salt, a metal salt, or a combination thereof.

9. The method of claim 1, wherein the pharmaceutically acceptable salt of the compound is a salt selected from the group consisting of $NH_4^+$, $Na^+$, $Li^+$, $K^+$, $Ca^{+2}$, $Mg^{+2}$, $Fe^{+2}$, $Fe^{+3}$, $Cu^{+2}$, $Al^{+3}$, $Zn^{+2}$, 2-trimethylethanolammonium cation (choline), or a quaternary salt of isopropylamine, trimethylamine, diethylamine, triethylamine, tripropylamine, ethanolamine, 2-dimethylaminoethanol, 2-diethylaminoethanol, lysine, arginine, and histidine.

10. The method of claim 1, wherein the urological inflammation comprises inflammation of the bladder, urethra, urothelium lining, prostate, vagina, uterus, or any combination thereof.

11. The method of claim 1, wherein the administration of the compound inhibits the activity of LL-37 in a subject.

* * * * *

UNITED STATES PATENT AND TRADEMARK OFFICE
CERTIFICATE OF CORRECTION

PATENT NO. : 9,522,162 B2
APPLICATION NO. : 14/006771
DATED : December 20, 2016
INVENTOR(S) : Glenn D. Prestwich et al.

Page 1 of 1

It is certified that error appears in the above-identified patent and that said Letters Patent is hereby corrected as shown below:

In the Specification

Please replace the paragraph at Column 1, Lines 19-22 with the following paragraph:

This invention was made with government support under Grants T32 HL079874 and DK093413 awarded by the National Institutes of Health. The government has certain rights in the invention.

Signed and Sealed this
Ninth Day of January, 2018

Joseph Matal
*Performing the Functions and Duties of the*
*Under Secretary of Commerce for Intellectual Property and*
*Director of the United States Patent and Trademark Office*